United States Patent
Shen et al.

(10) Patent No.: US 11,672,812 B2
(45) Date of Patent: Jun. 13, 2023

(54) METHODS AND COMPOSITIONS COMPRISING TYROSINE KINASE INHIBITOR AND TRIPTOLIDE FOR THE TREATMENT OF CANCER

(71) Applicant: City of Hope, Duarte, CA (US)

(72) Inventors: Binghui Shen, Duarte, CA (US); Li Zheng, Duarte, CA (US); Karen Reckamp, Duarte, CA (US); Ravi Salgia, Duarte, CA (US)

(73) Assignee: CITY OF HOPE, Duarte, CA (US)

( * ) Notice: Subject to any disclaimer, the term of this patent is extended or adjusted under 35 U.S.C. 154(b) by 126 days.

(21) Appl. No.: 17/225,970

(22) Filed: Apr. 8, 2021

(65) Prior Publication Data
US 2021/0315911 A1    Oct. 14, 2021

Related U.S. Application Data

(60) Provisional application No. 63/007,654, filed on Apr. 9, 2020.

(51) Int. Cl.
| | | |
|---|---|---|
| *A61K 31/665* | (2006.01) | |
| *A61K 31/517* | (2006.01) | |
| *A61P 35/00* | (2006.01) | |
| *A61K 31/506* | (2006.01) | |
| *A61K 31/585* | (2006.01) | |
| *A61K 31/5377* | (2006.01) | |

(52) U.S. Cl.
CPC ......... *A61K 31/665* (2013.01); *A61K 31/506* (2013.01); *A61K 31/517* (2013.01); *A61K 31/5377* (2013.01); *A61K 31/585* (2013.01); *A61P 35/00* (2018.01)

(58) Field of Classification Search
CPC .................................................. A61K 31/665
USPC ......................................................... 514/100
See application file for complete search history.

(56) References Cited

PUBLICATIONS

Tong et al, Chem. Pharm. Bull. (2019) vol. 67(8), pp. 864-871.*
Mak et al., Mol. Cancer Ther. (2009) vol. 8(9) pp. 2509-2516.*
Berge, S.M. et al. (Jan. 1977). "Pharmaceutical Salts", *Journal of Pharmaceutical Science* 66(1):1-19.
Jiao, L. et al. (Jul. 2019). "Chinese Herbal Medicine Combined with EGFR-TKI in EGFR Mutation-Positive Advanced Pulmonary Adenocarcinoma (CATLA): A Multicenter, Randomized, Double-Blind, Placebo-Controlled Trial," *Frontiers in Pharmacology* vol. 10, Article 732.
Li, F. et al. (May 2020, e-published Mar. 10, 2020). "Triptolide inhibits epithelial-mesenchymal transition and induces apoptosis in gefitinib-resistant lung cancer cells," *Oncology Reports* 43:1569-1579.
Tong, X. et al. (Aug. 1, 2019, e-published May 29, 2019). "Combined Treatment with Triptolide and Tyrosine Kinase Inhibitors Synergistically Enhances Apoptosis in Non-small Cell Lung Cancer H1975 Cells but Not H1299 Cells through EGFR/Akt Pathway," *Chem Pharm Bull* 67(8):864-871.

* cited by examiner

*Primary Examiner* — Taofiq A Solola
(74) *Attorney, Agent, or Firm* — Mintz, Levin, Cohn, Ferris, Glovsky and Popeo, P.C.

(57) ABSTRACT

Provided herein, inter alia, are methods, compositions and kits for treating cancer in a subject. The methods include administration of one or more tyrosine kinase inhibitors and triptolide or an analog thereof to the subject. The methods, compositions and kits are effective for preventing resistance and/or increasing sensitivity to tyrosine kinase inhibitors.

9 Claims, 6 Drawing Sheets

METHODS AND COMPOSITIONS COMPRISING TYROSINE KINASE INHIBITOR AND TRIPTOLIDE FOR THE TREATMENT OF CANCER

CROSS-REFERENCES TO RELATED APPLICATIONS

This application claims priority to U.S. Application No. 63/007,654 filed Apr. 9, 2020, the disclosure of which is incorporated by reference herein in its entirety.

BACKGROUND OF THE INVENTION

Non-small cell lung cancers (NSCLCs) harboring EGFR activating mutations initially respond to EGFR tyrosine kinase inhibitors (EGFR-TKIs), including Tagrisso (Osimertinib). However, acquired resistance to these drugs develops in almost all patients, most commonly due to new DNA mutations that arise during treatment. Provided herein, inter alia, are solutions to these and other problems in the art.

BRIEF SUMMARY OF THE INVENTION

Provided herein, inter alia, are methods, compositions and kits for treating cancer in a subject in need thereof. Applicant has discovered compositions including triptolide or analogs thereof are effective for treating subjects having cancer (e.g. non-small cell lung cancer, etc.), including cancers that are resistant, are at risk of developing resistance, or have decreased sensitivity to cancer therapeutics. The methods and compositions include administration of triptolide or an analog thereof to a subject, thereby treating the cancer and/or preventing resistance of the cancer to cancer therapeutics (e.g. TKIs). Compositions, methods and kits described herein can increase sensitivity or prevent resistance to TKIs (e.g. Osimertinib), which are commonly used to treat mutation-positive cancers, and further can have a synergistic effect when combined with TKIs.

Thus, in an aspect is provided a method of treating cancer in a subject in need thereof, the method including administering to the subject a therapeutically effective amount of a tyrosine kinase inhibitor (TKI) and triptolide or analog thereof.

In another aspect is provided a method of preventing resistance to a tyrosine kinase inhibitor (TKI) in a subject having cancer, the method including administering to the subject a therapeutically effective amount of triptolide or an analog thereof.

In another aspect is provided a pharmaceutical composition including a tyrosine kinase inhibitor (TKI), triptolide or an analog thereof, and a pharmaceutically acceptable excipient.

In an aspect a kit is provided, the kit including a first dosage unit form including a tyrosine kinase inhibitor (TKI), a second dosage unit form including triptolide or an analog thereof, and a pharmaceutically acceptable excipient.

DETAILED DESCRIPTION OF THE INVENTION

Figure 1:
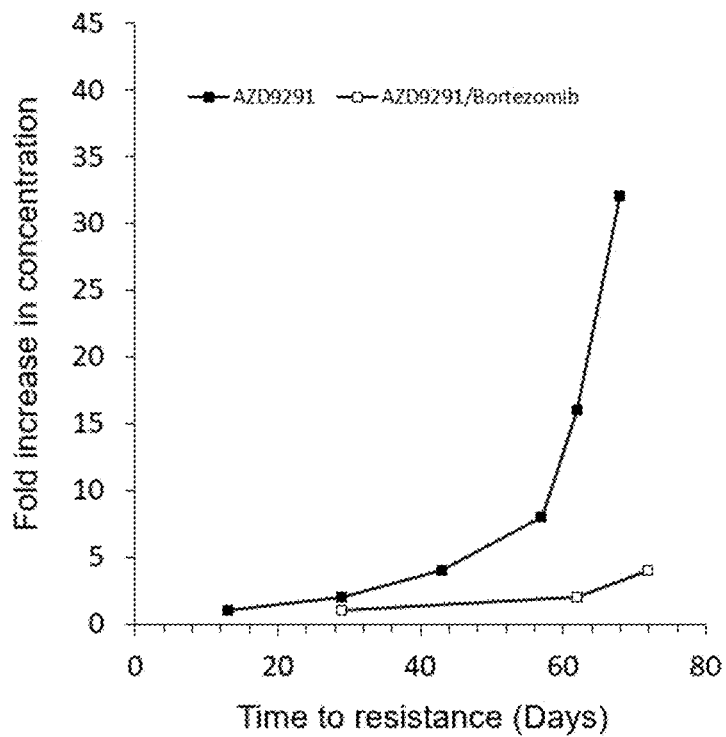
FIG. 1 is a graph showing the effect of Velcade (Bortezomib) on resistance development to Tagrisso (AZD9291) in HCC827 cells.

Provided herein are compositions and methods for treating cancer that include tyrosine kinase inhibitors and triptolide.

After reading this description it will become apparent to one skilled in the art how to implement the present disclosure in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present disclosure as set forth herein.

Before the present technology is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description divided into various sections only for the reader's convenience and disclosure found in any section may be combined with that in another section. Titles or subtitles may be used in the specification for the convenience of a reader, which are not intended to influence the scope of the present disclosure.

Definitions

Unless defined otherwise, all technical and scientific terms used herein have the same meaning as commonly understood by one of ordinary skill in the art to which this disclosure belongs. In this specification and in the claims that follow, reference will be made to a number of terms that shall be defined to have the following meanings:

The terminology used herein is for the purpose of describing particular embodiments only and is not intended to be limiting. As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to an amount means that the amount may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid. The terms "non-naturally occurring amino acid" and "unnatural amino acid" refer to amino acid analogs, synthetic amino acids, and amino acid mimetics which are not found in nature.

The term "amino acid side chain" refers to the functional substituent contained on amino acids. For example, an amino acid side chain may be the side chain of a naturally occurring amino acid. Naturally occurring amino acids are those encoded by the genetic code (e.g., alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, or valine), as well as those amino acids that are later modified, e.g., hydroxyproline, γ-carboxyglutamate, and O-phosphoserine. In embodiments, the amino acid side chain may be a non-natural amino acid side chain. In embodiments, the amino acid side chain is H,

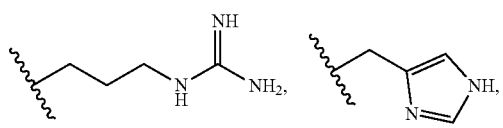

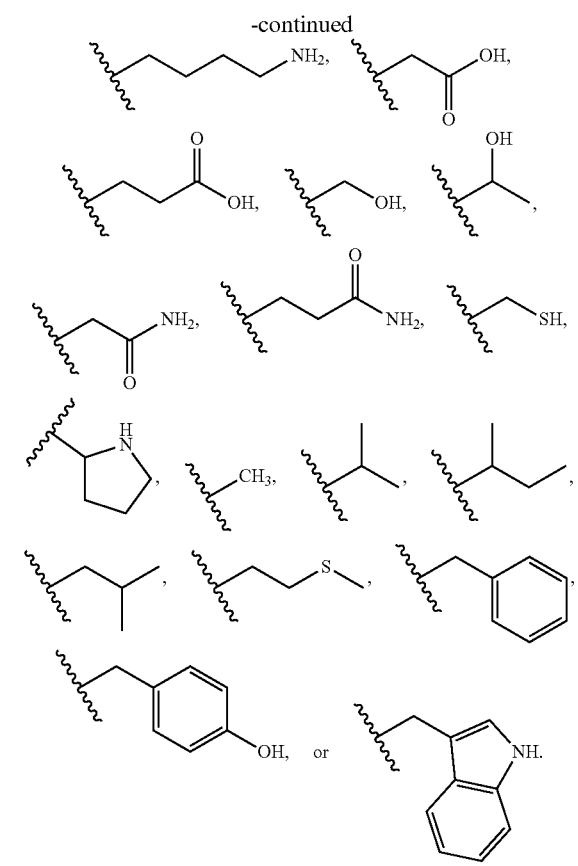

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "polypeptide," "peptide" and "protein" are used interchangeably herein to refer to a polymer of amino acid residues, wherein the polymer may in embodiments be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

"Percentage of sequence identity" is determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site http://www.ncbi.nlm.nih.gov/BLAST/ or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

An amino acid or nucleotide base "position" is denoted by a number that sequentially identifies each amino acid (or nucleotide base) in the reference sequence based on its position relative to the N-terminus (or 5'-end). Due to deletions, insertions, truncations, fusions, and the like that must be taken into account when determining an optimal alignment, in general the amino acid residue number in a test sequence determined by simply counting from the N-terminus will not necessarily be the same as the number of its corresponding position in the reference sequence. For example, in a case where a variant has a deletion relative to an aligned reference sequence, there will be no amino acid in the variant that corresponds to a position in the reference sequence at the site of deletion. Where there is an insertion in an aligned reference sequence, that insertion will not correspond to a numbered amino acid position in the reference sequence. In the case of truncations or fusions there can be stretches of amino acids in either the reference or aligned sequence that do not correspond to any amino acid in the corresponding sequence.

The terms "numbered with reference to" or "corresponding to," when used in the context of the numbering of a given amino acid or polynucleotide sequence, refers to the numbering of the residues of a specified reference sequence when the given amino acid or polynucleotide sequence is compared to the reference sequence.

For specific proteins described herein, the named protein includes any of the protein's naturally occurring forms, variants or homologs that maintain the protein transcription factor activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. In other embodiments, the protein is the protein as identified by its NCBI sequence reference. In other embodiments, the protein is the protein as identified by its NCBI sequence reference, homolog or functional fragment thereof.

A tyrosine kinase or tyrosine protein kinase is an enzyme that catalyzes a reaction in which a phosphate group from ATP is removed and is typically transferred to a protein. Tyrosine kinases are a subclass of protein kinases including serine and threonine kinases. Tyrosine kinases may function by transferring phosphate groups to the amino acid tyrosine. Phosphorylation of proteins by tyrosine kinases may assist in signal transduction and regulating cellular activity, including cell division. Tyrosine kinases include EGFR, VEGFR, Src, InsR, PDGFR, Abl, and c-Kit.

The term "EGFR protein" or "EGFR" as used herein includes any of the recombinant or naturally-occurring forms of epidermal growth factor receptor (EGFR) also known as ErbB-1 or HER1 in humans, or variants or homologs thereof that maintain EGFR activity (e.g. within at least 50%, 80%, 90%, 95%, 96%, 97%, 98%, 99% or 100% activity compared to EGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring EGFR protein. In embodiments, the EGFR protein is substantially identical to the protein identified by the UniProt reference number P00533 or a variant or homolog having substantial identity thereto. In embodiments, the EGFR protein includes a T790M mutation in reference to the EGFR sequence identified by the UniProt reference number P00533. In embodiments, the EGFR protein includes a E746-A750 deletion in reference to the EGFR sequence identified by the UniProt reference number P00533.

The term "VEGFR protein" or "VEGFR" as used herein includes any of the recombinant or naturally-occurring forms of vascular endothelial growth factor receptor (VEGFR) also known as vascular endothelial growth factor receptor 1, VEGFR-1, Fms-like tyrosine kinase 1, vascular endothelial growth factor receptor 2, VEGFR-2, Fms-like tyrosine kinase 2, vascular endothelial growth factor receptor 3, VEGFR-3, Fms-like tyrosine kinase 3, Tyrosine-protein kinase receptor FLT, or Vascular permeability factor receptor, or variants or homologs thereof that maintain VEGFR activity (e.g. within at least 50%, 80%, 90%, 95%, 96%, 97%, 98%, 99% or 100% activity compared to VEGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring VEGFR protein. In embodiments, the VEGFR protein is substantially identical to the protein identified by the UniProt reference number P17948 or a variant or homolog having substantial identity thereto. In embodiments, the VEGFR protein is substantially identical to the protein identified by the UniProt reference number P35968 or a variant or homolog having substantial identity thereto. In embodiments, the VEGFR protein is substantially identical to the protein identified by the UniProt reference number P35916 or a variant or homolog having substantial identity thereto.

The term "PDGFR protein" or "PDGFR" as used herein includes any of the recombinant or naturally-occurring forms of Platelet-derived growth factor receptors (PDGFR) also known as Platelet-derived growth factor receptor alpha, PDGFR-alpha, Platelet-derived growth factor receptor beta, PDGFR-beta, or variants or homologs thereof that maintain PDGFR activity (e.g. within at least 50%, 80%, 90%, 95%, 96%, 97%, 98%, 99% or 100% activity compared to PDGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring PDGFR protein. In embodiments, the PDGFR protein is substantially identical to the protein identified by the UniProt reference number P16234 or a variant or homolog having substantial identity thereto. In embodiments, the PDGFR protein is substantially identical to the protein identified by the Uni-Prot reference number P09619 or a variant or homolog having substantial identity thereto.

The term "InsR protein" or "InsR" as used herein includes any of the recombinant or naturally-occurring forms of Insulin receptor (InsR) also known as IR or CD220, or variants or homologs thereof that maintain InsR activity (e.g. within at least 50%, 80%, 90%, 95%, 96%, 97%, 98%, 99% or 100% activity compared to InsR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring InsR protein. In embodiments, the InsR protein is substantially identical to the protein identified by the UniProt reference number P06213 or a variant or homolog having substantial identity thereto.

The term "Src protein" or "Src" as used herein includes any of the recombinant or naturally-occurring forms of Proto-oncogene tyrosine-protein kinase Src (Src) also known as proto-oncogene c-Src or c-Src, or variants or homologs thereof that maintain Src activity (e.g. within at least 50%, 80%, 90%, 95%, 96%, 97%, 98%, 99% or 100% activity compared to Src). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Src protein. In embodiments, the Src protein is substantially identical to the protein identified by the UniProt reference number P12931 or a variant or homolog having substantial identity thereto.

The term "Abl protein" or "Abl" as used herein includes any of the recombinant or naturally-occurring forms of Tyrosine-protein kinase ABL1 (ABL1) also known as Abelson tyrosine-protein kinase 1, Proto-oncogene c-Abl or p150, or variants or homologs thereof that maintain Abl activity (e.g. within at least 50%, 80%, 90%, 95%, 96%, 97%, 98%, 99% or 100% activity compared to Abl). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Abl protein. In embodiments, the Abl protein is substantially identical to the protein identified by the UniProt reference number P00519 or a variant or homolog having substantial identity thereto.

The term "c-Kit protein" or "c-Kit" as used herein includes any of the recombinant or naturally-occurring forms of c-Kit also known as c-Kit protooncogene, or variants or homologs thereof that maintain c-Kit activity (e.g. within at least 50%, 80%, 90%, 95%, 96%, 97%, 98%, 99% or 100% activity compared to c-Kit). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring c-Kit protein. In embodiments, the c-Kit protein is substantially identical to the protein identified by the UniProt reference number Q15999 or a variant or homolog having substantial identity thereto.

The term "anaplastic lymphoma kinase protein" or "anaplastic lymphoma kinase" as used herein includes any of the recombinant or naturally-occurring forms of anaplastic lymphoma kinase (ALK) also known as ALK tyrosine kinase receptor, CD246, or variants or homologs thereof that maintain ALK activity (e.g. within at least 50%, 80%, 90%, 95%, 96%, 97%, 98%, 99% or 100% activity compared to ALK). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ALK protein. In embodiments, the ALK protein is substantially identical to the protein identified by the UniProt reference number Q9UM73 or a variant or homolog having substantial identity thereto.

The term "Proto-oncogene tyrosine-protein kinase ROS protein" or "Proto-oncogene tyrosine-protein kinase ROS" as used herein includes any of the recombinant or naturally-occurring forms of Proto-oncogene tyrosine-protein kinase ROS (ROS1) also known as Proto-oncogene c-Ros, Receptor tyrosine kinase c-ros oncogene 1, c-Ros receptor tyrosine kinase or variants or homologs thereof that maintain ROS1 activity (e.g. within at least 50%, 80%, 90%, 95%, 96%, 97%, 98%, 99% or 100% activity compared to ROS1). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring ROS1 protein. In embodiments, the ROS1 protein is substantially identical to the protein identified by the UniProt reference number P08922 or a variant or homolog having substantial identity thereto.

The term "fibroblast growth factor receptor protein" or "fibroblast growth factor receptor" as used herein includes any of the recombinant or naturally-occurring forms of fibroblast growth factor receptor (FGFR), or variants or homologs thereof that maintain FGFR activity (e.g. within at least 50%, 80%, 90%, 95%, 96%, 97%, 98%, 99% or 100% activity compared to FGFR). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring FGFR protein. In embodiments, the FGFR protein is substantially identical to the protein identified by the UniProt reference number P11362 or a variant or homolog having substantial identity thereto. In embodiments, the FGFR protein is substantially identical to the protein identified by the UniProt reference number P21802 or a variant or homolog having substantial identity thereto. In embodiments, the FGFR protein is substantially identical to the protein identified by the UniProt reference number P22607 or a variant or homolog having substantial identity thereto. In embodiments, the FGFR protein is substantially identical to the protein identified by the UniProt reference number P22455 or a variant or homolog having substantial identity thereto.

The term "Her2 protein" or "Her2" as used herein includes any of the recombinant or naturally-occurring forms of Receptor tyrosine-protein kinase erbB-2, also known as CD340 (cluster of differentiation 340), proto-oncogene Neu, Erbb2 (rodent), or ERBB2 (human), or variants or homologs thereof that maintain Her2 activity (e.g. within at least 50%, 80%, 90%, 95%, 96%, 97%, 98%, 99% or 100% activity compared to Her2). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Her2 protein. In embodiments, the Her2 protein is substantially identical to the protein identified by the UniProt reference number P04626 or a variant or homolog having substantial identity thereto.

The term "B-Raf proto-oncogene protein" or "B-Raf proto-oncogene" as used herein includes any of the recombinant or naturally-occurring forms of B-Raf proto-oncogene (BRAF), also known as B-Raf, serine/threonine-protein kinase B-Raf, p94, or variants or homologs thereof that maintain BRAF activity (e.g. within at least 50%, 80%, 90%, 95%, 96%, 97%, 98%, 99% or 100% activity compared to BRAF). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring BRAF protein. In embodiments, the BRAF protein is substantially identical to the protein identified by the UniProt reference number P15056 or a variant or homolog having substantial identity thereto.

The term "Mitogen-activated protein kinase protein" or "Mitogen-activated protein kinase" as used herein includes any of the recombinant or naturally-occurring forms of Mitogen-activated protein kinase (MAPK), also known as MAP kinase, extracellular signal-regulated kinases (ERK), or variants or homologs thereof that maintain MAPK activity (e.g. within at least 50%, 80%, 90%, 95%, 96%, 97%, 98%, 99% or 100% activity compared to MAPK). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MAPK protein. MAPK may refer to any of the protein kinases in the MAPK family, which are kinases specific to the amino acids serine and threonine. In embodiments, the MAPK protein is substantially identical to the protein identified by the UniProt reference number P28482 or a variant or homolog having substantial identity thereto. In embodiments, the MAPK protein is substantially identical to the protein identified by the UniProt reference number P27361 or a variant or homolog having substantial identity thereto. In embodiments, the MAPK protein is substantially identical to the protein identified by the UniProt reference number Q16659 or a variant or homolog having substantial identity thereto. In embodiments, the MAPK protein is substantially identical to the protein identified by the UniProt reference number P31152 or a variant or homolog having substantial identity thereto.

The term "neurotrophin tyrosine kinase receptor protein" or "neurotrophin tyrosine kinase receptor" as used herein includes any of the recombinant or naturally-occurring forms of neurotrophin tyrosine kinase receptor (NTRK), also known as Trk receptor, High affinity nerve growth factor receptor, or Tropomyosin-related kinase A, or variants or homologs thereof that maintain NTRK activity (e.g. within at least 50%, 80%, 90%, 95%, 96%, 97%, 98%, 99% or 100% activity compared to NTRK). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring NTRK protein. In embodiments, the NTRK protein is substantially identical to the protein identified by the UniProt reference number P04626 or a variant or homolog having substantial identity thereto. In embodiments, the NTRK protein is substantially identical to the protein identified by the UniProt reference number Q16620 or a variant or homolog having substantial identity thereto. In embodiments, the NTRK protein is substantially identical to the protein identified by the UniProt reference number Q16288 or a variant or homolog having substantial identity thereto.

The term "RET proto-oncogene protein" or "RET proto-oncogene" as used herein includes any of the recombinant or naturally-occurring forms of RET proto-oncogene (RET), also known as Proto-oncogene tyrosine-protein kinase receptor Ret, Cadherin family member 12, c-Ret, or variants or homologs thereof that maintain RET activity (e.g. within at least 50%, 80%, 90%, 95%, 96%, 97%, 98%, 99% or 100% activity compared to RET). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring RET protein. In embodiments, the RET protein is substantially identical to the protein identified by the UniProt reference number P07949 or a variant or homolog having substantial identity thereto. In embodiments, the RET protein is substantially identical to the protein identified by the UniProt reference number A0A024R7T2 or a variant or homolog having substantial identity thereto.

The term "B-Raf proto-oncogene protein" or "B-Raf proto-oncogene" as used herein includes any of the recombinant or naturally-occurring forms of B-Raf proto-oncogene (BRAF), also known as B-Raf, serine/threonine-protein kinase B-Raf, p94, or variants or homologs thereof that maintain BRAF activity (e.g. within at least 50%, 80%, 90%, 95%, 96%, 97%, 98%, 99% or 100% activity compared to BRAF). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring BRAF protein. In embodiments, the BRAF protein is substantially identical to the protein identified by the UniProt reference number P15056 or a variant or homolog having substantial identity thereto.

The term "Mesenchymal epithelial transition factor receptor protein" or "Mesenchymal epithelial transition factor receptor" as used herein includes any of the recombinant or naturally-occurring forms of Mesenchymal epithelial transition factor receptor (MET), also known as Hepatocyte growth factor receptor, HGF receptor, HGF/SF receptor, Proto-oncogene c-Met, or variants or homologs thereof that maintain MET activity (e.g. within at least 50%, 80%, 90%, 95%, 96%, 97%, 98%, 99% or 100% activity compared to MET). In some aspects, the variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MET protein. In embodiments, the MET protein is substantially identical to the protein identified by the UniProt reference number P08581 or a variant or homolog having substantial identity thereto.

The terms "disease" or "condition" refer to a state of being or health status of a patient or subject capable of being treated with the compounds or methods provided herein. The disease may be a cancer.

As used herein, the term "cancer" refers to all types of cancer, neoplasm or malignant tumors found in mammals (e.g. humans), including leukemias, lymphomas, carcinomas and sarcomas. Exemplary cancers that may be treated with a composition or method provided herein include breast cancer, colon cancer, lung cancer, leukemia, thyroid cancer, liver cancer, melanoma, skin cancer, kidney cancer, bladder cancer and head and neck cancer. Additional examples include, endocrine system cancers, brain cancer, cervix cancer, ovarian cancer, pancreatic cancer, cancers of the rectum, stomach cancer, cancers of the uterus, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is an EGFR-expressing cancer. In embodiments, the cancer is a EGFR-expressing cancer wherein EGFR includes a mutation. For example, the EGFR mutation can be a EGFR activating mutation. In instances, the EGFR mutation confers resistance of said cancer to an anti-cancer therapeutic (e.g. EGFR TKIs, etc.).

As used herein, the terms "metastasis," "metastatic," and "metastatic cancer" can be used interchangeably and refer to the spread of a proliferative disease or disorder, e.g., cancer, from one organ or another non-adjacent organ or body part. Cancer occurs at an originating site, e.g., breast, which site is referred to as a primary tumor, e.g., primary breast cancer. Some cancer cells in the primary tumor or originating site acquire the ability to penetrate and infiltrate surrounding normal tissue in the local area and/or the ability to penetrate the walls of the lymphatic system or vascular system circulating through the system to other sites and tissues in the body. A second clinically detectable tumor formed from cancer cells of a primary tumor is referred to as a metastatic or secondary tumor. When cancer cells metastasize, the metastatic tumor and its cells are presumed to be similar to those of the original tumor. Thus, if lung cancer metastasizes to the breast, the secondary tumor at the site of the breast consists of abnormal lung cells and not abnormal breast cells. The secondary tumor in the breast is referred to a metastatic lung cancer. Thus, the phrase metastatic cancer refers to a disease in which a subject has or had a primary tumor and has one or more secondary tumors. The phrases non-metastatic cancer or subjects with cancer that is not metastatic refers to diseases in which subjects have a primary tumor but not one or more secondary tumors. For example, metastatic lung cancer refers to a disease in a subject with or with a history of a primary lung tumor and with one or more secondary tumors at a second location or multiple locations, e.g., in the breast.

The terms "treating", or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. The term "treating" and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions are administered to the subject in an amount and for a duration sufficient to treat the patient. In embodiments, the treating or treatment is no prophylactic treatment.

The term "prevent" refers to a decrease in the occurrence of disease symptoms in a patient. As indicated above, the prevention may be complete (no detectable symptoms) or partial, such that fewer symptoms are observed than would likely occur absent treatment.

"Patient" or "subject in need thereof" refers to a living organism suffering from or prone to a disease (e.g. cancer) or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, a patient is human.

A "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, Dosage Calculations (1999); and *Remington: The Science and Practice of Pharmacy,* 20th Edition, 2003, Gennaro, Ed., Lippincott, Williams & Wilkins).

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

The term "therapeutically effective amount," as used herein, refers to that amount of the therapeutic agent sufficient to ameliorate the disorder, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as "-fold" increase or decrease. For example, a therapeutically effective amount can have at least a 1.2-fold, 1.5-fold, 2-fold, 5-fold, or more effect over a control.

Dosages may be varied depending upon the requirements of the patient and the compound being employed. The dose administered to a patient, in the context of the present disclosure, should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached. Dosage amounts and intervals can be adjusted individually to provide levels of the administered compound effective for the particular clinical indication being treated. This will provide a therapeutic regimen that is commensurate with the severity of the individual's disease state.

As used herein, the term "administering" means oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent. In embodiments, the administering does not include administration of any anti-cancer agent other than the recited agents (e.g. a TKI and/or triptolide (or analog thereof)).

"Co-administer" it is meant that a composition described herein is administered at the same time, just prior to, or just after the administration of one or more additional therapies. The compounds provided herein can be administered alone or can be coadministered to the patient. Coadministration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

As used herein, "sequential administration" includes that the administration of two agents (e.g., the compounds or compositions described herein) occurs separately on the same day or do not occur on a same day (e.g., occurs on consecutive days).

As used herein, "concurrent administration" includes overlapping in duration at least in part. For example, when two agents (e.g., any of the agents or class of agents described herein that has bioactivity) are administered concurrently, their administration occurs within a certain desired time. The agents administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The bioactive agents/agents do not have to be taken at the same time each day to include concurrent administration.

As used herein, "intermittent administration" includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization.

"Biological sample" or "sample" refer to materials obtained from or derived from a subject or patient. A biological sample includes sections of tissues such as biopsy and autopsy samples, and frozen sections taken for histological purposes. Such samples include bodily fluids such as blood and blood fractions or products (e.g., serum, plasma, platelets, red blood cells, and the like), sputum, tissue, cultured cells (e.g., primary cultures, explants, and transformed cells) stool, urine, synovial fluid, joint tissue, synovial tissue, synoviocytes, fibroblast-like synoviocytes, macrophage-like synoviocytes, immune cells, hematopoietic cells, fibroblasts, macrophages, T cells, etc. A biological sample is typically obtained from a eukaryotic organism, such as a mammal such as a primate e.g., chimpanzee or human; cow; dog; cat; a rodent, e.g., guinea pig, rat, mouse; rabbit; or a bird; reptile; or fish.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a compound as described herein (including embodiments and examples).

A "control" or "standard control" refers to a sample, measurement, or value that serves as a reference, usually a known reference, for comparison to a test sample, measurement, or value. For example, a test sample can be taken from a patient suspected of having a given disease (e.g. cancer) and compared to a known normal (non-diseased) individual (e.g. a standard control subject). A standard control can also represent an average measurement or value gathered from a population of similar individuals (e.g. standard control subjects) that do not have a given disease (i.e. standard control population), e.g., healthy individuals with a similar medical background, same age, weight, etc. A standard control value can also be obtained from the same individual, e.g. from an earlier-obtained sample from the patient prior to disease onset. For example, a control can be devised to compare therapeutic benefit based on pharmacological data (e.g., half-life) or therapeutic measures (e.g., comparison of side effects). Controls are also valuable for determining the significance of data. For example, if values for a given parameter are widely variant in controls, variation in test samples will not be considered as significant. One of skill will recognize that standard controls can be designed for assessment of any number of parameters (e.g. RNA levels, protein levels, specific cell types, specific bodily fluids, specific tissues, etc).

One of skill in the art will understand which standard controls are most appropriate in a given situation and be able to analyze data based on comparisons to standard control values. Standard controls are also valuable for determining the significance (e.g. statistical significance) of data. For example, if values for a given parameter are widely variant in standard controls, variation in test samples will not be considered as significant.

Cancer model organism, as used herein, is an organism exhibiting a phenotype indicative of cancer, or the activity of cancer causing elements, within the organism. The term cancer is defined above. A wide variety of organisms may serve as cancer model organisms, and include for example, cancer cells and mammalian organisms such as rodents (e.g. mouse or rat) and primates (such as humans). Cancer cell lines are widely understood by those skilled in the art as cells exhibiting phenotypes or genotypes similar to in vivo cancers. Cancer cell lines as used herein includes cell lines from animals (e.g. mice) and from humans.

"Contacting" is used in accordance with its plain ordinary meaning and refers to the process of allowing at least two distinct species (e.g. chemical compounds including biomolecules or cells) to become sufficiently proximal to react, interact or physically touch. It should be appreciated; however, the resulting reaction product can be produced directly from a reaction between the added reagents or from an intermediate from one or more of the added reagents that can be produced in the reaction mixture.

The term "contacting" may include allowing two species to react, interact, or physically touch, wherein the two species may be a compound as described herein and a protein or enzyme. In some embodiments contacting includes allowing a compound described herein to interact with a protein or enzyme that is involved in a signaling pathway.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "modulator" refers to a composition that increases or decreases the level of a target molecule or the function of a target molecule or the physical state of the target of the molecule relative to the absence of the modulator.

The term "modulate" is used in accordance with its plain ordinary meaning and refers to the act of changing or varying one or more properties. "Modulation" refers to the process of changing or varying one or more properties. For example, as applied to the effects of a modulator on a target protein, to modulate means to change by increasing or decreasing a property or function of the target molecule or the amount of the target molecule.

The terms "inhibitor," "repressor" or "antagonist" or "downregulator" interchangeably refer to a substance capable of detectably decreasing the expression or activity of a given gene or protein. The inhibitor can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the inhibitor.

A "therapeutic agent" as referred to herein, is a composition useful in treating or preventing a disease such as cancer (e.g., leukemia). In embodiments, the therapeutic agent is an anti-cancer agent. "Anti-cancer agent" is used in accordance with its plain ordinary meaning and refers to a composition (e.g. compound, drug, antagonist, inhibitor, modulator) having antineoplastic properties or the ability to inhibit the growth or proliferation of cells. In embodiments, an anti-cancer agent is a chemotherapeutic. In embodiments, an anti-cancer agent is an agent identified herein having utility in methods of treating cancer. In embodiments, an anti-cancer agent is an agent approved by the FDA or similar regulatory agency of a country other than the USA, for treating cancer.

"Anti-cancer agent" and "anticancer agent" are used in accordance with their plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. In some embodiments, the anti-cancer agent is a TKI.

A "tyrosine kinase inhibitor" or "TKI" is a molecule that decreases the activity of at least one tyrosine kinase enzyme. A TKI may be used to treat cancer, and thus may be an anti-cancer agent. A TKI may block phosphorylation of tyrosine residues. A TKI may compete with binding of adenosine triphosphate (ATP), the substrate, or both ATP and the substrate. A TKI inhibitor may act in an allosteric fashion by binding to a site outside the active site. A TKI may prevent tyrosine kinases from accessing the Cdc37-Hsp90 molecular chaperone system, leading to ubiquitylation and degradation of the tyrosine kinase. TKIs include but are not limited to acalabrutinib (Calquence), afatinib (Gilotrif), alectinib (Alecensa), avapritinib, axitinib (Inlyta), bosutinib (Bosulif), cabozantinib (Cabometyx, Cometriq), crizotinib (Xalkori), dacomitinib (Vizimpro), dasatinib (Spryrel), entrectinib (Rozlytrek), erlotinib (Tarceva), gilteritinib (Xospata), ibrutinib (Imbruvica), Imatinib (Glivec), lapatinib (Tykerb), midostaurin (Rydapt), neratinib (Nerlynx), Nilotinib (Tasigna), pacritinib, pazopanib (Votrieni), pexidartinib (Turalio), ponatinib (Iclusig), quizartinib, regorafenib (Stivarga), sorafenib (Nexavar), sunitinib (Sutent), vandetanib (Caprelsa), vemurafenib, zanubrutinib (Brukinsa), or ziv-aflibercept (Zaltrap).

A "multi-kinase inhibitor" is a small molecule inhibitor of at least one protein kinase, including tyrosine protein kinases and serine/threonine kinases. For example, a TKI may interact with multiple tyrosine protein kinases and inhibit or decrease their activity. Multi-kinase inhibitors may block phosphorylation. Multi-kinases inhibitors may act as covalent modifiers of protein kinases. Multi-kinase inhibitors may bind to the kinase active site or to a secondary or tertiary site, thereby inhibiting protein kinase activity. Multi-kinase inhibitors include dasatinib, sunitinib, erlotinib, bevacizumab, vatalanib, vemurafenib, vandetanib, cabozantinib, poatinib, axitinib, ruxolitinib, regorafenib, crizotinib, bosutinib, cetuximab, gefitinib, imatinib, lapatinib, lenvatinib, mubritinib, nilotinib, panitumumab, pazopanib, trastuzumab, or sorafenib.

Epithelial growth factor receptor (EGFR) tyrosine kinase inhibitor (TKI) refers to a compound that modulates or inhibits the activity of the EGFR protein. An EGFR TKI may decrease EGFR activity 10%, 20%, 30%, 40%, 50%, 60%, 70%, 80%, 90% or more in comparison to EGFR in the absence of the EGFR TKI. In the presence of an EGFR TKI, EGFR activity may be 1.5-fold, 2-fold, 3-fold, 4-fold, 5-fold, 10-fold or lower than EGFR activity in the absence of the EGFR TKI. EGFR TKIs include afatinib, dacomitinib, gefitinib, erlotinib and icotinib. EGFR TKIs may reversibly bind to EGFR and inhibit the binding of ATP to the domain, thereby inhibiting EGFR activity. EGFR TKIs may be irreversible inhibitors, which covalently bind to EGFR, thereby inhibiting EGFR activity.

Platelet-derived growth factor receptor (PDGFR) tyrosine kinase inhibitor (TKI) refers to a compound that modulates or inhibits the activity of the PDGFR protein. A PDGFR TKI may decrease PDGFR activity 10%, 20%, 30%, 40%, 50%, 60%, 70%, 80%, 90% or more in comparison to PDGFR in the absence of the PDGFR TKI. In the presence of a PDGFR TKI, EGFR activity may be 1.5-fold, 2-fold, 3-fold, 4-fold, 5-fold, 10-fold or lower than PDGFR activity in the absence of the PDGFR TKI. PDGFR TKIs include nilotinib, imatinib and sunitinib.

Vascular endothelial growth factor receptor (VEGFR) tyrosine kinase inhibitor (TKI) refers to a compound that modulates or inhibits the activity of the VEGFR protein. A VEGFR TKI may decrease VEGFR activity 10%, 20%, 30%, 40%, 50%, 60%, 70%, 80%, 90% or more in comparison to VEGFR in the absence of the VEGFR TKI. In the presence of a VEGFR TKI, VEGFR activity may be 1.5-fold, 2-fold, 3-fold, 4-fold, 5-fold, 10-fold or lower than VEGFR activity in the absence of the VEGFR TKI. VEGF TKIs include pazopanib, sorafenib, ponatinib, sunitinib, and axitinib.

Src tyrosine kinase inhibitor (TKI) refers to a compound that modulates or inhibits the activity of the Src protein. A Src TKI may decrease Src activity 10%, 20%, 30%, 40%, 50%, 60%, 70%, 80%, 90% or more in comparison to Src in the absence of the Src TKI. In the presence of a Src TKI, Src activity may be 1.5-fold, 2-fold, 3-fold, 4-fold, 5-fold, 10-fold or lower than Src activity in the absence of the Src TKI. Src TKIs include nilotinib, imatinib and sunitinib. Src TKIs include bosutinib, saracatinib, and dasatinib.

Abl tyrosine kinase inhibitor (TKI) refers to a compound that modulates or inhibits the activity of the Abl protein. An Abl TKI may decrease Abl activity 10%, 20%, 30%, 40%, 50%, 60%, 70%, 80%, 90% or more in comparison to Abl in the absence of the Abl TKI. In the presence of a Abl TKI, Abl activity may be 1.5-fold, 2-fold, 3-fold, 4-fold, 5-fold, 10-fold or lower than Abl activity in the absence of the Abl TKI. Abl TKIs include dasatinib, bosutinib, ponatinib, and bafetinib. Abl TKIs may bind to the kinase domain of Abl when the kinase domain is in a closed or inactive conformation, thereby occluding the substrate binding site and disrupting the ATP phosphate binding site, thereby inhibiting Abl activity. Able TKIs may bind to the active conformation of the kinase domain, thereby inhibiting Abl activity.

Insulin receptor (InsR) tyrosine kinase inhibitor (TKI) refers to a compound that modulates or inhibits the activity of the InsR protein. A InsR TKI may decrease InsR activity 10%, 20%, 30%, 40%, 50%, 60%, 70%, 80%, 90% or more in comparison to InsR in the absence of the InsR TKI. In the presence of a InsR TKI, InsR activity may be 1.5-fold, 2-fold, 3-fold, 4-fold, 5-fold, 10-fold or lower than InsR activity in the absence of the InsR TKI. InsR TKIs include linsitinib and ceritinib.

c-Kit tyrosine kinase inhibitor (TKI) refers to a compound that modulates or inhibits the activity of the c-Kit protein. A c-Kit TKI may decrease c-Kit activity 10%, 20%, 30%, 40%, 50%, 60%, 70%, 80%, 90% or more in comparison to c-Kit in the absence of the c-Kit TKI. In the presence of a c-Kit TKI, c-Kit activity may be 1.5-fold, 2-fold, 3-fold, 4-fold, 5-fold, 10-fold or lower than c-Kit activity in the absence of the c-Kit TKI. c-Kit TKIs include pexidartinib, imatinib and avapritinib.

Anaplastic lymphoma kinase (ALK) TKI refers to a compound that modulates or inhibits the activity of the ALK protein. An ALK TKI may decrease ALK activity 10%, 20%, 30%, 40%, 50%, 60%, 70%, 80%, 90% or more in comparison to ALK in the absence of the ALK TKI. In the presence of an ALK TKI, ALK activity may be 1.5-fold, 2-fold, 3-fold, 4-fold, 5-fold, 10-fold or lower than ALK activity in the absence of the ALK TKI. ALK TKIs include ceritinib, alectinib, brigatinib, lorlatinib, entrectinib, crizotinib, Tesaro, Teva, or Xcovery.

ROS proto-oncogene 1 (ROS1) TKI refers to a compound that modulates or inhibits the activity of the ROS1 protein. A ROS1 TKI may decrease ROS1 activity 10%, 20%, 30%, 40%, 50%, 60%, 70%, 80%, 90% or more in comparison to ROS1 in the absence of the ROS1 TKI. In the presence of an ROS1 TKI, ROS1 activity may be 1.5-fold, 2-fold, 3-fold, 4-fold, 5-fold, 10-fold or lower than ROS1 activity in the absence of the ROS1 TKI. ROS1 TKIs include crizotinib, entrectinib, lorlatinib, ceritinib, TPX-0005, DS-6051b, or cabozantinib.

Fibroblast growth factor receptor (FGFR) TKI refers to a compound that modulates or inhibits the activity of the FGFR protein. A FGFR TKI may decrease c-Kit activity 10%, 20%, 30%, 40%, 50%, 60%, 70%, 80%, 90% or more in comparison to c-Kit in the absence of the FGFR TKI. In the presence of a FGFR TKI, FGFR activity may be 1.5-fold, 2-fold, 3-fold, 4-fold, 5-fold, 10-fold or lower than FGFR activity in the absence of the FGFR TKI. FGFR TKIs include PD173074, dovitinib, Ki23057, lenvatinib, brivanib, nintedanib, ponatinib, MK-2461, lucitanib, or AZD4547.

Human epidermal growth factor receptor 2 (HER2) TKI refers to a compound that modulates or inhibits the activity of the HER2 protein. A HER2 TKI may decrease HER2 activity 10%, 20%, 30%, 40%, 50%, 60%, 70%, 80%, 90% or more in comparison to HER2 in the absence of the HER2 TKI. In the presence of a HER2 TKI, HER2 activity may be 1.5-fold, 2-fold, 3-fold, 4-fold, 5-fold, 10-fold or lower than HER2 activity in the absence of the HER2 TKI. HER2 TKIs include lapatinib, neratinib, dacomitinib, afatinib, AZD8931, AST1306, AEE788, canertinib, CP724,714, CUDC101, TAK285, aelitinib, or AC480.

B-Raf proto-oncogene (BRAF) TKI, refers to a compound that modulates or inhibits the activity of the BRAF protein. A BRAF TKI may decrease BRAF activity 10%, 20%, 30%, 40%, 50%, 60%, 70%, 80%, 90% or more in comparison to BRAF in the absence of the BRAF TKI. In the presence of a BRAF TKI, BRAF activity may be 1.5-fold, 2-fold, 3-fold, 4-fold, 5-fold, 10-fold or lower than BRAF activity in the absence of the BRAF TKI. BRAF TKIs include vemurafenib, dabrafenib, or encorafenib.

Mitogen-activated protein kinase (MAPK) TKI, refers to a compound that modulates or inhibits the activity of the MAPK protein. A MAPK TKI may decrease MAPK activity 10%, 20%, 30%, 40%, 50%, 60%, 70%, 80%, 90% or more in comparison to MAPK in the absence of the MAPK TKI. In the presence of a MAPK TKI, MAPK activity may be 1.5-fold, 2-fold, 3-fold, 4-fold, 5-fold, 10-fold or lower than MAPK activity in the absence of the MAPK TKI. MAPK TKIs include sorafenib, SB590885, PLX4720, XL281, RAF265, encorafenib, dabrafenib, cobimetinib, binimetinib, selumetinib, or trametinib.

Neurotrophin tyrosine kinase receptor (NTRK) TKI refers to a compound that modulates or inhibits the activity of the NTRK protein. A NTRK TKI may decrease NTRK activity 10%, 20%, 30%, 40%, 50%, 60%, 70%, 80%, 90% or more in comparison to NTRK in the absence of the NTRK TKI. In the presence of a NTRK TKI, NTRK activity may be 1.5-fold, 2-fold, 3-fold, 4-fold, 5-fold, 10-fold or lower than NTRK activity in the absence of the NTRK TKI. NTRK TKIs include entrectinib or larotrectinib.

RET proto-oncogene (RET) TKI refers to a compound that modulates or inhibits the activity of the RET protein. A RET TKI may decrease RET activity 10%, 20%, 30%, 40%, 50%, 60%, 70%, 80%, 90% or more in comparison to RET in the absence of the RET TKI. In the presence of a RET TKI, RET activity may be 1.5-fold, 2-fold, 3-fold, 4-fold, 5-fold, 10-fold or lower than RET activity in the absence of the RET TKI. RET TKIs include nintedanib, vandetanib, or alectinib.

Mesenchymal-epithelial transition (MET) TKI refers to a compound that modulates or inhibits the activity of the MET protein. A MET TKI may decrease MET activity 10%, 20%, 30%, 40%, 50%, 60%, 70%, 80%, 90% or more in comparison to MET in the absence of the MET TKI. In the presence of a MET TKI, MET activity may be 1.5-fold, 2-fold, 3-fold, 4-fold, 5-fold, 10-fold or lower than MET activity in the absence of the MET TKI. MET TKIs include crizotinib, tivantinib, savolitinib, cabozantinib, foretinib, tepotinib or capmatinib.

The term "associated" or "associated with" in the context of a substance or substance activity or function associated with a disease (e.g. a protein associated disease, a cancer (e.g., lung cancer)) means that the disease (e.g. cancer) is caused by (in whole or in part), or a symptom of the disease is caused by (in whole or in part) the substance or substance activity or function. As used herein, what is described as being associated with a disease, if a causative agent, could be a target for treatment of the disease.

The term "aberrant" as used herein refers to different from normal. When used to describe enzymatic activity or protein function, aberrant refers to activity or function that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The term "pharmaceutically acceptable salts" is meant to include salts of the active compounds that are prepared with relatively nontoxic acids or bases, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present disclosure contain both basic and acidic functionalities that allow the compounds to be converted into either base or acid addition salts.

In addition to salt forms, the present disclosure provides compounds, which are in a prodrug form. Prodrugs of the compounds described herein are those compounds that readily undergo chemical changes under physiological conditions to provide the compounds of the present disclosure. Prodrugs of the compounds described herein may be converted in vivo after administration. Additionally, prodrugs can be converted to the compounds of the present disclosure by chemical or biochemical methods in an ex vivo environment, such as, for example, when contacted with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the disclosure. One of skill in the art will recognize that other pharmaceutical excipients are useful in the present disclosure.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

"Analog," or "analogue" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound. Accordingly, an analog is a compound that is similar or comparable in function and appearance but not in structure or origin to a reference compound. For example, an analog may refer to an analog of the triptolide molecule.

Triptolide is a small molecule produced by the thunder god vine, *Tripterygium wilfordii*. Triptolide is a diterpenoid epoxide, and may exert immunosuppressive, anti-inflammatory, and/or anti-tumorigenic effects. The structure of Triptolide is shown in Table 1.

A triptolide analog refers to a chemical compound that may be structurally similar to triptolide, e.g., in the replacement of one atom by an atom of a different element, or in the presence of a particular functional group, or the replacement of one functional group by another functional group, or the absolute stereochemistry of one or more chiral centers of the reference compound. A triptolide analog refers to a compound that may be similar or comparable in function and appearance but not in structure or origin to triptolide. Triptolide analogs include but are not limited to triptolide 0-Methyl Phosphate Disodium Salt (minnelide), (5R)-5 hydroxy triptolide, 14b-fluoro triptolide, MRx102 and PG490-88. The structures of triptolide and several triptolide analogs are shown in Table 1.

TABLE 1

Structures of triptolide and triptolide analogs

| Compound | Structure | Structure No. |
|---|---|---|
| Triptolide | 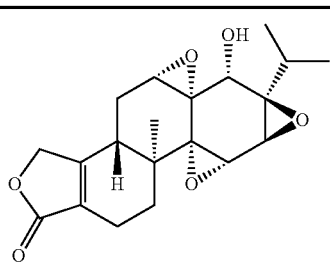 | 1 |

TABLE 1-continued

Structures of triptolide and triptolide analogs

| Compound | Structure | Structure No. |
|---|---|---|
| Triptolide O-Methyl Phosphate Disodium Salt (Minnelide) | 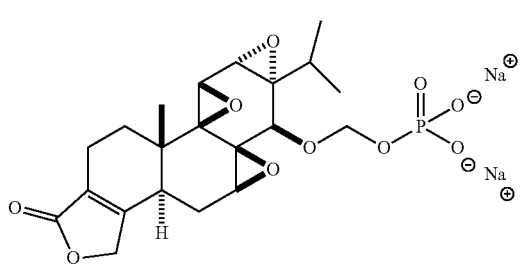 | 2 |
| (5R)-5 hydroxy Triptolide | 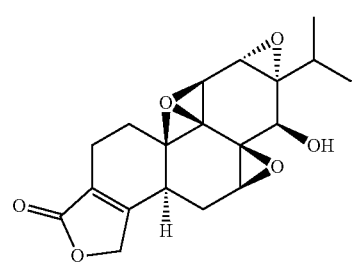 | 3 |
| 14b-Fluoro triptolide | 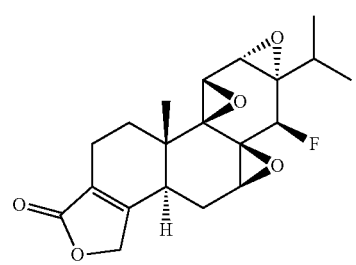 [SMILES: CC(C)[C@]12O[C@H]1[C@@H]1O[C@]13[C@]1(O[C@H]1C[C@H]1C4=C(CC[C@@]13C)C(=O)OC4)[C@@H]2F] | 4 |
| MRx102 | 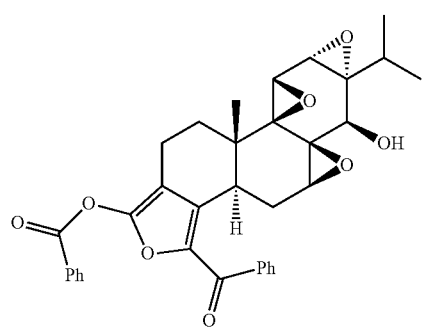 [SMILES: CC(C)[C@]12O[C@H]1[C@@H]1O[C@]13[C@]1(O[C@H]1C[C@H]1c4c(C(=O)c5ccccc5)oc(OC(=O)c5ccccc5)c4CC[C@@]13C)[C@@H]2O] | 5 |
| PG490-88 | 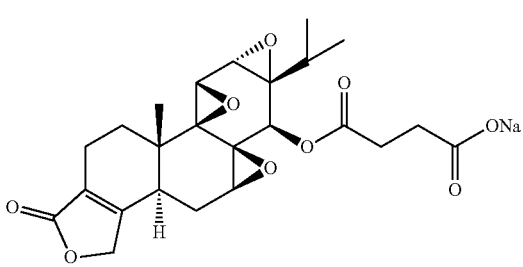 | 6 |

Methods of Treatment

In embodiments, the methods provided herein including embodiments thereof are contemplated to be effective for treating cancer (e.g. EGFR expressing cancer, cancers expressing mutated EGFR, lung cancer, etc.) in a subject in need thereof, wherein the cancer may be resistant, have decreased sensitivity, or is at risk of developing resistance or decreased sensitivity to anti-cancer agents (e.g. tyrosine kinase inhibitors). In embodiments, the methods described herein can sensitize the cancer to anti-cancer agents, reverse the resistance or decreased sensitivity to anti-cancer agents, and/or prevent or inhibit resistance development of the cancer to anti-cancer agents.

Thus, in an aspect is provided a method of treating cancer in a subject in need thereof. The method includes administering to the subject a therapeutically effective amount of a tyrosine kinase inhibitor (TKI) and triptolide or an analog thereof. In embodiments, the method includes administering to the subject a therapeutically effective amount of a tyrosine kinase inhibitor (TKI) and triptolide. In embodiments, the method includes administering to the subject a therapeutically effective amount of a tyrosine kinase inhibitor (TKI) and a triptolide analog. In embodiments, the administering does not include administration of any anti-cancer agent other than the recited agents (e.g. a TKI and/or triptolide (or analog thereof)). In embodiments, the administering does not include administration of active pharmaceutical agent other than the recited agents (e.g. a TKI and/or triptolide (or analog thereof)).

In embodiments, the TKI is an epithelial growth factor receptor (EGFR) TKI, an anaplastic lymphoma kinase (ALK) TKI, a ROS proto-oncogene 1 (ROS1) TKI, a platelet derived growth factor receptor (PDGFR) TKI, a vascular endothelial growth factor receptor (VEGFR) TKI, an insulin receptor (InsR) TKI, a Src TKI, a c-Kit TKI, a fibroblast growth factor receptor (FGFR) TKI, a human epidermal growth factor receptor 2 (HER2) TKI, a B-Raf proto-oncogene (BRAF) TKI, a mitogen-activated protein kinase (MAPK) TKI, a neurotrophin tyrosine kinase receptor (NTRK) TKI, a RET proto-oncogene (RET) TKI, a mesenchymal-epithelial transition (MET) TKI, or an Abl TKI. In embodiments, the TKI is an EGFR TKI. In embodiments, the TKI is an ALK TKI. In embodiments, the TKI is an ROS1 TKI. In embodiments, the TKI is a PDGFR TKI. In embodiments, the TKI is a VEGFR TKI. In embodiments, the TKI is an InsR TKI. In embodiments, the TKI is a Src TKI. In embodiments, the TKI is a c-Kit TKI. In embodiments, the TKI is a FGFR TKI. In embodiments, the TKI is a HER2 TKI. In embodiments, the TKI is a BRAF TKI. In embodiments, the TKI is a MAPK TKI. In embodiments, the TKI is an NTRK TKI. In embodiments, the TKI is a RET TKI. In embodiments, the TKI is a MET TKI. In embodiments, the TKI is an Abl TKI.

In embodiments, the TKI is acalabrutinib (Calquence). In embodiments, the TKI is afatinib (Gilotrif). In embodiments, the TKI is alectinib (Alecensa). In embodiments, the TKI is avapritinib. In embodiments, the TKI is axitinib (Inlyta). In embodiments, the TKI is bosutinib (Bosulif). In embodiments, the TKI is cabozantinib (Cabometyx, Cometriq). In embodiments, the TKI is crizotinib (Xalkori). In embodiments, the TKI is dacomitinib (Vizimpro). In embodiments, the TKI is dasatinib (Sprycel) In embodiments, the TKI is entrectinib (Rozlytrek). In embodiments, the TKI is erlotinib (Tarceva). In embodiments, the TKI is gilteritinib (Xospata). In embodiments, the TKI is ibrutinib (Imbruvica). In embodiments, the TKI is imatinib (Glivec). In embodiments, the TKI is lapatinib (Tykerb). In embodiments, the TKI is midostaurin (Rydapt). In embodiments, the TKI is neratinib (Nerlynx). In embodiments, the TKI is nilotinib (Tasigna). In embodiments, the TKI is pacritinib. In embodiments, the TKI is pazopanib (Votrient) In embodiments, the TKI is pexidartinib (Turalio). In embodiments, the TKI is ponatinib (Iclusig). In embodiments, the TKI is quizartinib. In embodiments, the TKI is regorafenib (Stivarga). In embodiments, the TKI is sorafenib (Nexavar). In embodiments, the TKI is sunitinib (Sutent). In embodiments, the TKI is vandetanib (Caprelsa). In embodiments, the TKI is vemurafenib. In embodiments, the TKI is zanubrutinib (Brukinsa). In embodiments, the TKI is ziv-aflibercept (Zaltrap). In embodiments the EGFR TKI is osimertinib (Tagrisso). In embodiments, the TKI is a salt (e.g. osimertinib mesylate, etc.) of any one of the TKIs provided herein. In embodiments, the methods include administering more than one TKI with triptolide or an analog thereof.

In embodiments, the triptolide analog is triptolide O-methyl phosphate disodium salt (minnelide), (5R)-5 hydroxy triptolide, 14b-fluoro triptolide, MRx102, or PG490-88. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of an EGFR TKI and triptolide or an analog thereof. In embodiments, the method includes administering to the subject a therapeutically effective amount of an EGFR TKI and triptolide. In embodiments, the method include administering to the subject a therapeutically effective amount of an EGFR TKI and a triptolide analog. In embodiments the EGFR TKI is osimertinib (Tagrisso), erlotinib (Tarceva), gefitinib, or afatinib. In embodiments, the EGFR TKI is osimertinib. In embodiments, the EGFR TKI is erlotinib. In embodiments, the EGFR TKI is gefitinib. In embodiments, the EGFR TKI is afatinib. The structure of several EGFR TKIs are shown in Table 2.

TABLE 2

Structures of EGFR TKIs

| EGFR TKI | Structure | Structure No. |
|---|---|---|
| Osimertinib | 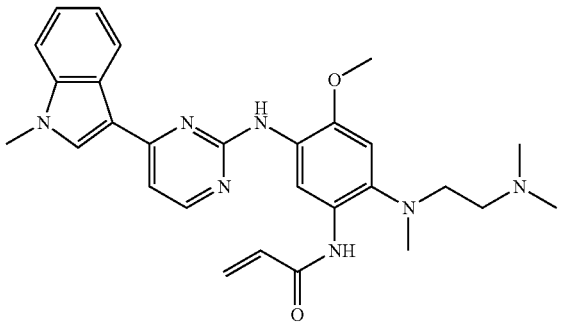 | 7 |

TABLE 2-continued

Structures of EGFR TKIs

| EGFR TKI | Structure | Structure No. |
|---|---|---|
| Erlotinib | [chemical structure] | 8 |
| Gefitinib | [chemical structure] | 9 |
| Afatinib | [chemical structure] | 10 |

In embodiments, the triptolide analog is minnelide, (5R)-5 hydroxy triptolide, 14b-fluoro triptolide, MRx102, or PG490-88. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a PDGFR TKI and triptolide or an analog thereof. In embodiments, the method includes administering to the subject a therapeutically effective amount of a PDGFR TKI and triptolide. In embodiments, the method includes administering to the subject a therapeutically effective amount of a PDGFR TKI and a triptolide analog. In embodiments, the PDGFR TKI is nilotinib. In embodiments, the PDGFR TKI is imatinib. In embodiments, the PDGFR TKI is sunitinib. In embodiments, the triptolide analog is minnelide, (5R)-5 hydroxy triptolide, 14b-fluoro triptolide, MRx102, or PG490-88. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a VEGFR TKI and triptolide or an analog thereof. In embodiments, the method includes administering to the subject a therapeutically effective amount of an VEGFR TKI and triptolide. In embodiments, the method includes administering to the subject a therapeutically effective amount of an VEGFR TKI and a triptolide analog. In embodiments, the VEGFR TKI is pazopanib. In embodiments, the VEGFR TKI is sorafenib. In embodiments, the VEGFR TKI is ponatinib. In embodiments, the VEGFR TKI is sunitinib. In embodiments, the VEGFR TKI is axitinib. In embodiments, the triptolide analog is minnelide, (5R)-5 hydroxy triptolide, 14b-fluoro triptolide, MRx102, or PG490-88. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a Src TKI and triptolide or an analog thereof. In embodiments, the method includes administering to the subject a therapeutically effective amount of a Src TKI and triptolide. In embodiments, the method includes administering to the subject a therapeutically effective amount of a Src TKI and a triptolide analog.

In embodiments, the Src TKI is nilotinib. In embodiments, the Src TKI is imatinib. In embodiments, the Src TKI is sunitinib. In embodiments, the Src TKI is bosutinib. In embodiments, the Src TKI is saracatinib. In embodiments, the Src TKI is dasatinib. In embodiments, the triptolide analog is minnelide, (5R)-5 hydroxy triptolide, 14b-fluoro triptolide, MRx102, or PG490-88. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to a subject in need thereof a therapeutically effective amount of an Abl TKI and triptolide or an analog thereof. In embodiments, the method includes administering to the subject a therapeutically effective amount of an Abl TKI and triptolide. In embodiments, the method includes administering to the subject a therapeutically effective amount of an Abl TKI and a triptolide analog. In embodiments, the Abl TKI is dasatinib. In embodiments, the Abl TKI is bosutinib. In embodiments, the Abl TKI is ponatinib. In embodiments, the Abl TKI is bafetinib. In embodiments, the triptolide analog is minnelide, (5R)-5 hydroxy triptolide, 14b-fluoro triptolide, MRx102, or PG490-88. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering a therapeutically effective amount of an InsR TKI and triptolide or an analog thereof. In embodiments, the method includes administering to the subject a therapeutically effective amount of an InsR TKI and triptolide. In embodiments, the method includes administering to the subject a therapeutically effective amount of an InsR TKI and a triptolide analog. In embodiments, the InsR TKI is linsitinib. In embodiments, the InsR TKI is ceritinib. In embodiments, the triptolide analog is minnelide, (5R)-5 hydroxy triptolide, 14b-fluoro triptolide, MRx102, or PG490-88. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to a subject a therapeutically effective amount of a c-Kit TKI and triptolide or an analog thereof. In embodiments, the method includes administering to a subject a therapeutically effective amount of a c-Kit TKI and triptolide. In embodiments, the method includes administering to the subject a therapeutically effective amount of a c-Kit TKI and a triptolide analog. In embodiments, the c-Kit TKI is pexidartinib. In embodiments, the c-Kit TKI is imatinib. In embodiments, the c-Kit TKI is avapritinib. In embodiments, the triptolide analog is minnelide, (5R)-5 hydroxy triptolide, 14b-fluoro triptolide, MRx102, or PG490-88. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to a subject a therapeutically effective amount of a ALK TKI and triptolide or an analog thereof. In embodiments, the method provided herein includes administering to a subject a therapeutically effective amount of a ALK TKI and triptolide. In embodiments, the method includes administering to the subject a therapeutically effective amount of a ALK TKI and a triptolide analog. In embodiments, the ALK TKI is ceritinib. In embodiments, the ALK TKI is alectinib. In embodiments, the ALK TKI is brigatinib. In embodiments, the ALK TKI is lorlatinib. In embodiments, the ALK TKI is entrectinib. In embodiments, the ALK TKI is crizotinib. In embodiments, the ALK TKI is TSR-011 (Tesaro). In embodiments, the ALK TKI is CEP-37440 (Teva). In embodiments, the ALK TKI is X-396 (Xcovery). In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a ROS1 TKI and triptolide or an analog thereof. In embodiments, the method includes administering to the subject a therapeutically effective amount of a ROS1 TKI and triptolide. In embodiments, the method includes administering to the subject a therapeutically effective amount of a ROS1 TKI and a triptolide analog. In embodiments, the ROS1 TKI is crizotinib. In embodiments, the ROS1 TKI is entrectinib. In embodiments, the ROS1 TKI is lorlatinib. In embodiments, the ROS1 TKI is ceritinib. In embodiments, the ROS1 TKI is TPX-0005. In embodiments, the ROS1 TKI is DS-6051b. In embodiments, the ROS1 TKI is cabozantinib. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a FGFR TKI and triptolide or an analog thereof. In embodiments, the method includes administering to the subject a therapeutically effective amount of a FGFR TKI and triptolide. In embodiments, the method includes administering to the subject a therapeutically effective amount of a FGFR TKI and a triptolide analog. In embodiments, the FGFR TKI is PD173074. In embodiments, the FGFR TKI is dovitinib. In embodiments, the FGFR TKI is Ki23057. In embodiments, the FGFR TKI is lenvatinib. In embodiments, the FGFR TKI is brivanib. In embodiments, the FGFR TKI is nintedanib. In embodiments, the FGFR TKI is ponatinib. In embodiments, the FGFR TKI is MK-2461. In embodiments, the FGFR TKI is lucitanib. In embodiments, the FGFR TKI is AZD4547. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a HER2 TKI and triptolide or an analog thereof. In embodiments, the method includes administering to the subject a therapeutically effective amount of a HER2 TKI and triptolide. In embodiments, the method includes administering to the subject a therapeutically effective amount of a HER2 TKI and a triptolide analog. In embodiments, the HER2 TKI is lapatinib. In embodiments, the HER2 TKI is neratinib. In embodiments, the HER2 TKI is dacomitinib. In embodiments, the HER2 TKI is afatinib. In embodiments, the HER2 TKI is AZD8931. In embodiments, the HER2 TKI is AST1306. In embodiments, the HER2 TKI is AEE788. In embodiments, the HER2 TKI is canertinib. In embodiments, the HER2 TKI is CP724,714. In embodiments, the HER2 TKI is CUDC101. In embodiments, the HER2 TKI is TAK285. In embodiments, the HER2 TKI is aelitinib. In embodiments, the HER2 TKI is AC480. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a BRAF TKI and triptolide or an analog thereof. In embodiments, the method includes administering to the subject a therapeutically effective amount of a BRAF TKI and triptolide. In embodiments, the method includes administering to the subject a therapeutically effective amount of a BRAF TKI and a triptolide analog. In embodiments, the BRAF TKI is vemurafenib. In embodiments, the BRAF TKI is dabrafenib. In embodiments, the BRAF TKI is encorafenib. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a MAPK TKI and triptolide or an analog thereof. In embodiments, the method includes administering to the subject a therapeutically effective amount of a MAPK TKI and triptolide. In embodiments, the method includes administering to the subject a therapeutically effective amount of a MAPK TKI and a triptolide analog. In embodiments, the MAPK TKI is sorafenib. In embodiments, the MAPK TKI is SB590885. In embodiments, the MAPK TKI is PLX4720. In embodiments, the MAPK TKI is XL281. In embodiments, the MAPK TKI is RAF265. In embodiments, the MAPK TKI is encorafenib. In embodiments, the MAPK TKI is dabrafenib. In embodiments, the MAPK TKI is cobimetinib. In embodiments, the MAPK TKI is binimetinib. In embodiments, the MAPK TKI is selumetinib. In embodiments, the MAPK TKI is trametinib. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a NTRK TKI and triptolide or an analog thereof. In embodiments, the method includes administering to the subject a therapeutically effective amount of a NTRK TKI and triptolide. In embodiments, the method includes administering to the subject a therapeutically effective amount of a NTRK TKI and a triptolide analog. In embodiments, the NTRK TKI is entrectinib. In embodiments, the NTRK TKI is larotrectinib. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a RET TKI and triptolide or an analog thereof. In embodiments, the method includes administering to the subject a therapeutically effective amount of a RET TKI and triptolide. In embodiments, the method includes administering to the subject a therapeutically effective amount of a RET TKI and a triptolide analog. In embodiments, the RET TKI is Nintedanib. In embodiments, the RET TKI is vandetanib. In embodiments, the RET TKI is alectinib. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method includes administering to the subject a therapeutically effective amount of a MET TKI and triptolide, or an analog thereof. In embodiments, the method includes administering to the subject a therapeutically effective amount of a MET TKI and triptolide. In embodiments, the method includes administering to the subject a therapeutically effective amount of a MET TKI and a triptolide analog. In embodiments, the MET TKI is crizotinib. In embodiments, the MET TKI is tivantinib. In embodiments, the MET TKI is savolitinib. In embodiments, the MET TKI is cabozantinib. In embodiments, the MET TKI is foretinib. In embodiments, the MET TKI is tepotinib. In embodiments, the MET TKI is capmatinib. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In embodiments, the method provided herein includes administering to the subject a therapeutically effective amount of a tyrosine kinase inhibitor (TKI) and triptolide, as described above, wherein the combination has synergistic effect. In embodiments, the methods include administering to the subject a therapeutically effective amount of a tyrosine kinase inhibitor (TKI) and a triptolide analog, as described above, wherein the combination has synergistic effect. In embodiments, the synergistic effect is more than a sum of effects from individual administration of the TKI or triptolide or analog thereof.

In instances, the synergistic effect is cancer cell death. Cancer cell death can be quantified, for example, by a decrease in tumor volume or decrease in the number of cancer cells. In embodiments, the cancer is an EGFR expressing cancer (e.g. non-small cell lung cancer). In embodiments, the cancer is an EGFR expressing cancer, wherein EGFR includes a mutation (e.g. T790M, E746 A750 deletion, etc.). In embodiments, synergy between the TKI (e.g. Osimertinib, Erlotinib, etc.) and triptolide or an analog thereof may result in about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater decrease in tumor volume or number of cancer cells than the sum of the decrease when the TKI (e.g. Osimertinib, Erlotinib, etc.) and triptolide or an analog thereof are used individually and separately.

In embodiments, synergy between the TKI (e.g. Osimertinib, Erlotinib, etc.) and triptolide or an analog thereof may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of tyrosine kinase (e.g. EGFR, etc.) activity than the sum of the inhibition when the TKI (e.g. Osimertinib, Erlotinib, etc.) and triptolide or an analog thereof are used individually and separately.

In instances, the synergistic effect is inhibition of metastasis of cancer in a subject. In embodiments, the cancer is an EGFR expressing cancer (e.g. non-small cell lung cancer). In embodiments, the cancer is an EGFR expressing cancer, wherein EGFR includes a mutation (e.g. T790M, E746-A750 deletion, etc.). In embodiments, synergy between the TKI (e.g. Osimertinib, Erlotinib, etc.) and triptolide or an analog thereof may result in 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% greater inhibition of metastasis of a cancer in a subject than the sum of the inhibition when the TKI (e.g. Osimertinib Erlotinib, etc.) and triptolide or an analog thereof are used individually and separately.

For the method provided herein, in embodiments, the effective amount of a TKI and the effective amount of triptolide or analog thereof are a combined additive amount. In embodiments, the effective amount of a TKI and the effective amount of triptolide or analog thereof are a combined synergistic amount. In embodiments, the TKI and triptolide or analog thereof are administered sequentially or simultaneously.

A "synergistic amount" as used herein refers to the sum of a first amount (e.g., a TKI) and a second amount (e.g., triptolide or analog there) that results in a synergistic effect (i.e. an effect greater than an additive effect). Therefore, the terms "synergy", "synergism", "synergistic", "combined synergistic amount", and "synergistic therapeutic effect" which are used herein interchangeably, refer to a measured effect of the compound administered in combination where the measured effect is greater than the sum of the individual effects of each of the compounds provided herein administered alone as a single agent. More specifically, a "combined synergistic amount" is a combined amount of a first agent (e.g. a tyrosine kinase inhibitor (TKI)) and second agent (e.g. triptolide) effective to provide a synergistic effect (e.g. for treating cancer, including embodiments described herein). In embodiments, the methods herein including administering TKI and triptolide (or analog thereof), include administering a combined synergistic amount of the TKI and triptolide (or analog thereof). In embodiments, the pharmaceutical compositions herein including a TKI and triptolide (or analog thereof), include a combined synergistic amount of the TKI and triptolide (or analog thereof).

In embodiments, a synergistic amount may be about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10.0, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% of the amount of the TKI provided herein when used separately from triptolide or analog thereof.

The methods provided herein including embodiments thereof, the treatment for cancer causes a reduction in tumor volume or tumor volume growth, or other indicia of cancer growth inhibition or reduction. In embodiments, the methods can reduce tumor volume or tumor volume growth or other indicia of cancer activity 10%, 20%, 30%, 40%, 50%, 60%, 70%, 80%, 90% or more in comparison to a control in the absence of said methods. In embodiments, the methods can reduce tumor volume or tumor volume growth or other indicia of cancer activity 1.5-fold, 2-fold, 3-fold, 4-fold, 5-fold, 10-fold or lower in comparison to a control in the absence of said methods. In embodiments, the methods can reduce tumor volume or tumor volume growth or other indicia of cancer activity 10%, 20%, 30%, 40%, 50%, 60%, 70%, 80%, 90% or more in comparison to treatment with a tyrosine kinase inhibitor (TKI), triptolide or a triptolide analog. In embodiments, the methods can reduce tumor volume or tumor volume growth or other indicia of cancer activity 1.5-fold, 2-fold, 3-fold, 4-fold, 5-fold, 10-fold or lower in comparison to a treatment with a tyrosine kinase inhibitor (TKI), triptolide or a triptolide analog.

For the method provided herein, in embodiments, the cancer is breast cancer, colon cancer, lung cancer, leukemia, thyroid cancer, liver cancer, melanoma, skin cancer, kidney cancer, bladder cancer or head and neck cancer. In embodiments, the cancer is breast cancer. In embodiments, the cancer is colon cancer. In embodiments, the cancer is lung cancer. In embodiments, the cancer is leukemia. In embodiments, the cancer is thyroid cancer. In embodiments, the cancer is liver cancer. In embodiments, the cancer is melanoma. In embodiments, the cancer is skin cancer. In embodiments, the cancer is kidney cancer. In embodiments, the cancer is bladder cancer. In embodiments, the cancer is head and neck cancer. In embodiments, the lung cancer is non-small cell lung carcinoma. In embodiments, the cancer is a chemotherapeutic resistant cancer.

For the method provided herein, in embodiments, the subject has been previously treated for cancer. In embodiments, the subject previously treated for cancer was previously administered a TKI (e.g. an EGFR TKI, etc.) and has discontinued administration of the TKI. In embodiments, discontinuation of the TKI is due to resistance or decreased sensitivity to the TKI.

In embodiments, the method includes simultaneous administration of the therapeutically effective amount of the tyrosine kinase inhibitor (TKI) and triptolide or an analog thereof, wherein the administration includes separate pharmaceutical formulations or a single pharmaceutical formulation. In embodiments, the method includes simultaneous administration using separate pharmaceutical formulations. In embodiments, the method includes simultaneous administration using a single pharmaceutical formulation. In embodiments, the method includes consecutive administration of the therapeutically effective amount of the tyrosine kinase inhibitor (TKI) and triptolide or an analog thereof in either order, where there may be a time period when both (or all) active agents simultaneously exert their biological activities. Preparation and dosing schedules for such chemotherapeutic agents may be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). Thus, for the method provided herein, in embodiments, the TKI and triptolide or analog thereof are administered sequentially. In embodiments, the TKI and triptolide or analog thereof are administered simultaneously.

For the method provided herein, in embodiments, the TKI is administered at an amount from about 5 mg to about 300 mg. In embodiments, the TKI is administered at an amount from about 10 mg to about 300 mg. In embodiments, the TKI is administered at an amount from about 15 mg to about 300 mg. In embodiments, the TKI is administered at an amount from about 20 mg to about 300 mg. In embodiments, the TKI is administered at an amount from about 25 mg to about 300 mg. In embodiments, the TKI is administered at an amount from about 30 mg to about 300 mg. In embodiments, the TKI is administered at an amount from about 35 mg to about 300 mg. In embodiments, the TKI is administered at an amount from about 40 mg to about 300 mg. In embodiments, the TKI is administered at an amount from about 45 mg to about 300 mg. In embodiments, the TKI is administered at an amount from about 50 mg to about 300 mg. In embodiments, the TKI is administered at an amount from about 55 mg to about 300 mg. In embodiments, the TKI is administered at an amount from about 60 mg to about 300 mg. In embodiments, the TKI is administered at an amount from about 65 mg to about 300 mg. In embodiments, the TKI is administered at an amount from about 70 mg to about 300 mg. In embodiments, the TKI is administered at an amount from about 75 mg to about 300 mg. In embodiments, the TKI is administered at an amount from about 80 mg to about 300 mg. In embodiments, the TKI is administered at an amount from about 85 mg to about 300 mg. In embodiments, the TKI is administered at an amount from about 90 mg to about 300 mg. In embodiments, the TKI is administered at an amount from about 95 mg to about 300 mg. In embodiments, the TKI is administered at an amount from about 100 mg to about 300 mg. In embodiments, the TKI is administered at an amount from about 105 mg to about 300 mg. In embodiments, the TKI is administered at an amount from about 110 mg to about 300 mg. In embodiments, the TKI is administered at an amount from about 115 mg to about 300 mg. In embodiments, the TKI is administered at an amount from about 120 mg to about 300 mg. In embodiments, the TKI is administered at an amount from about 125 mg to about 300 mg. In embodiments, the TKI is administered at an amount from about 130 mg to about 300 mg. In embodiments, the TKI is administered at an amount from about 135 mg to about 300 mg. In embodiments, the TKI is administered at an amount from about 140 mg to about 300 mg. In embodiments, the TKI is administered at an amount from about 145 mg to about 300 mg. In embodiments, the TKI is administered at an amount from about 150 mg to about 300 mg. In embodiments, the TKI is administered at an amount from about 155 mg to about 300 mg. In embodiments, the TKI is administered at an amount from about 160 mg to about 300 mg. In embodiments, the TKI is administered at an amount from about 165 mg to about 300 mg. In embodiments, the TKI is administered at an amount from about 170 mg to about 300 mg. In embodiments, the TKI is administered at an amount from about 175 mg to about 300 mg. In embodiments, the TKI is administered at an amount from about 180 mg to about 300 mg. In embodiments, the TKI is administered at an amount from about 185 mg to about 300 mg. In embodiments, the TKI is administered at an amount from about 190 mg to about 300 mg. In embodiments, the TKI is administered at an amount from about 195 mg to about 300 mg. In embodiments, the TKI is administered at an amount from about 200 mg to about 300 mg. In embodiments, the TKI is administered at an amount from about 205 mg to about 300 mg. In embodiments, the TKI is administered at an amount from about 210 mg to about 300 mg. In embodiments, the TKI is administered at an amount from about 215 mg to about 300 mg. In embodiments, the TKI is administered at an amount from about 220 mg to about 300 mg. In embodiments, the TKI is administered at an amount from about 225 mg to about 300 mg. In embodiments, the TKI is administered at an amount from about 230 mg to about 300 mg. In embodiments, the TKI is administered at an amount from about 235 mg to about 300 mg. In embodiments, the TKI is administered at an amount from about 240 mg to about 300 mg. In embodiments, the TKI is administered at an amount from about 245 mg to about 300 mg. In embodiments, the TKI is administered at an amount from about 250 mg to about 300 mg. In embodiments, the TKI is administered at an amount from about 255 mg to about 300 mg. In embodiments, the TKI is administered at an amount from about 260 mg to about 300 mg. In embodiments, the TKI is administered at an amount from about 265 mg to about 300 mg. In embodiments, the TKI is administered at an amount from about 270 mg to about 300 mg. In embodiments, the TKI is administered at an amount from about 275 mg to about 300 mg. In embodiments, the TKI is administered at an amount from about 280 mg to about 300 mg. In embodiments, the TKI is administered at an amount from about 285 mg to about 300 mg. In embodiments, the TKI is administered at an amount from about 290 mg to about 300 mg. In embodiments, the TKI is administered at an amount from about 295 mg to about 300 mg.

In embodiments, the TKI is administered at an amount from about 5 mg to about 295 mg. In embodiments, the TKI is administered at an amount from about 5 mg to about 290 mg. In embodiments, the TKI is administered at an amount from about 5 mg to about 285 mg. In embodiments, the TKI is administered at an amount from about 5 mg to about 280 mg. In embodiments, the TKI is administered at an amount from about 5 mg to about 275 mg. In embodiments, the TKI is administered at an amount from about 5 mg to about 270 mg. In embodiments, the TKI is administered at an amount from about 5 mg to about 265 mg. In embodiments, the TKI is administered at an amount from about 5 mg to about 260 mg. In embodiments, the TKI is administered at an amount from about 5 mg to about 255 mg. In embodiments, the TKI is administered at an amount from about 5 mg to about 250 mg. In embodiments, the TKI is administered at an amount from about 5 mg to about 245 mg. In embodiments, the TKI is administered at an amount from about 5 mg to about 240 mg. In embodiments, the TKI is administered at an amount from about 5 mg to about 235 mg. In embodiments, the TKI is administered at an amount from about 5 mg to about 230 mg. In embodiments, the TKI is administered at an amount from about 5 mg to about 225 mg. In embodiments, the TKI is administered at an amount from about 5 mg to about 220 mg. In embodiments, the TKI is administered at an amount from about 5 mg to about 215 mg. In embodiments, the TKI is administered at an amount from about 5 mg to about 210 mg. In embodiments, the TKI is administered at an amount from about 5 mg to about 205 mg. In embodiments, the TKI is administered at an amount from about 5 mg to about 200 mg. In embodiments, the TKI is administered at an amount from about 5 mg to about 195 mg. In embodiments, the TKI is administered at an amount from about 5 mg to about 190 mg. In embodiments, the TKI is administered at an amount from about 5 mg to about 185 mg. In embodiments, the TKI is administered at an amount from about 5 mg to about 180 mg. In embodiments, the TKI is administered at an amount from about 5 mg to about 175 mg. In embodiments, the TKI is administered at an amount from about 5 mg to about 170 mg. In embodiments, the TKI is administered at an amount from about 5 mg to about 165 mg. In embodiments, the TKI is administered at an amount from about 5 mg to about 160 mg. In embodiments, the TKI is administered at an amount from about 5 mg to about 155 mg. In embodiments, the TKI is administered at an amount from about 5 mg to about 150 mg. In embodiments, the TKI is administered at an amount from about 5 mg to about 145 mg. In embodiments, the TKI is administered at an amount from about 5 mg to about 140 mg. In embodiments, the TKI is administered at an amount from about 5 mg to about 135 mg. In embodiments, the TKI is administered at an amount from about 5 mg to about 130 mg. In embodiments, the TKI is administered at an amount from about 5 mg to about 125 mg. In embodiments, the TKI is administered at an amount from about 5 mg to about 120 mg. In embodiments, the TKI is administered at an amount from about 5 mg to about 115 mg. In embodiments, the TKI is administered at an amount from about 5 mg to about 110 mg. In embodiments, the TKI is administered at an amount from about 5 mg to about 105 mg. In embodiments, the TKI is administered at an amount from about 5 mg to about 100 mg. In embodiments, the TKI is administered at an amount from about 5 mg to about 95 mg. In embodiments, the TKI is administered at an amount from about 5 mg to about 90 mg. In embodiments, the TKI is administered at an amount from about 5 mg to about 85 mg. In embodiments, the TKI is administered at an amount from about 5 mg to about 80 mg. In embodiments, the TKI is administered at an amount from about 5 mg to about 75 mg. In embodiments, the TKI is administered at an amount from about 5 mg to about 70 mg. In embodiments, the TKI is administered at an amount from about 5 mg to about 65 mg. In embodiments, the TKI is administered at an amount from about 5 mg to about 60 mg. In embodiments, the TKI is administered at an amount from about 5 mg to about 55 mg. In embodiments, the TKI is administered at an amount from about 5 mg to about 50 mg. In embodiments, the TKI is administered at an amount from about 5 mg to about 45 mg. In embodiments, the TKI is administered at an amount from about 5 mg to about 40 mg. In embodiments, the TKI is administered at an amount from about 5 mg to about 35 mg. In embodiments, the TKI is administered at an amount from about 5 mg to about 30 mg. In embodiments, the TKI is administered at an amount from about 5 mg to about 25 mg. In embodiments, the TKI is administered at an amount from about 5 mg to about 20 mg. In embodiments, the TKI is administered at an amount from about 5 mg to about 15 mg. In embodiments, the TKI is administered at an amount from about 5 mg to about 10 mg. In embodiments, the TKI is administered at an amount of about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg.

In embodiments, the TKI is administered at an amount from about 5 mg to about 150 mg. In embodiments, the TKI is administered at an amount from about 10 mg to about 150 mg. In embodiments, the TKI is administered at an amount from about 15 mg to about 150 mg. In embodiments, the TKI is administered at an amount from about 20 mg to about 150 mg. In embodiments, the TKI is administered at an amount from about 25 mg to about 150 mg. In embodiments, the TKI is administered at an amount from about 30 mg to about 150 mg. In embodiments, the TKI is administered at an amount from about 35 mg to about 150 mg. In embodiments, the TKI is administered at an amount from about 40 mg to about 150 mg. In embodiments, the TKI is administered at an amount from about 45 mg to about 150 mg. In embodiments, the TKI is administered at an amount from about 50 mg to about 150 mg. In embodiments, the TKI is administered at an amount from about 55 mg to about 150 mg. In embodiments, the TKI is administered at an amount from about 60 mg to about 150 mg. In embodiments, the TKI is administered at an amount from about 65 mg to about 150 mg. In embodiments, the TKI is administered at an amount from about 70 mg to about 150 mg. In embodiments, the TKI is administered at an amount from about 75 mg to about 150 mg. In embodiments, the TKI is administered at an amount from about 80 mg to about 150 mg. In embodiments, the TKI is administered at an amount from about 85 mg to about 150 mg. In embodiments, the TKI is administered at an amount from about 90 mg to about 150 mg. In embodiments, the TKI is administered at an amount from about 95 mg to about 150 mg. In embodiments, the TKI is administered at an amount from about 100 mg to about 150 mg. In embodiments, the TKI is administered at an amount from about 105 mg to about 150 mg. In embodiments, the TKI is administered at an amount from about 110 mg to about 150 mg. In embodiments, the TKI is administered at an amount from about 115 mg to about 150 mg. In embodiments, the TKI is administered at an amount from about 120 mg to about 150 mg. In embodiments, the TKI is administered at an amount from about 125 mg to about 150 mg. In embodiments, the TKI is administered at an amount from about 130 mg to about 150 mg. In embodiments, the TKI is administered at an amount from about 135 mg to about 150 mg. In embodiments, the TKI is administered at an amount from about 140 mg to about 150 mg. In embodiments, the TKI is administered at an amount from about 145 mg to about 150 mg.

In embodiments, the TKI is administered at an amount from about 5 mg to about 145 mg. In embodiments, the TKI is administered at an amount from about 5 mg to about 140 mg. In embodiments, the TKI is administered at an amount from about 5 mg to about 135 mg. In embodiments, the TKI is administered at an amount from about 5 mg to about 130 mg. In embodiments, the TKI is administered at an amount from about 5 mg to about 125 mg. In embodiments, the TKI is administered at an amount from about 5 mg to about 120 mg. In embodiments, the TKI is administered at an amount from about 5 mg to about 115 mg. In embodiments, the TKI is administered at an amount from about 5 mg to about 110 mg. In embodiments, the TKI is administered at an amount from about 5 mg to about 105 mg. In embodiments, the TKI is administered at an amount from about 5 mg to about 100 mg. In embodiments, the TKI is administered at an amount from about 5 mg to about 95 mg. In embodiments, the TKI is administered at an amount from about 5 mg to about 90 mg. In embodiments, the TKI is administered at an amount from about 5 mg to about 85 mg. In embodiments, the TKI is administered at an amount from about 5 mg to about 80 mg. In embodiments, the TKI is administered at an amount from about 5 mg to about 75 mg. In embodiments, the TKI is administered at an amount from about 5 mg to about 70 mg. In embodiments, the TKI is administered at an amount from about 5 mg to about 65 mg. In embodiments, the TKI is administered at an amount from about 5 mg to about 60 mg. In embodiments, the TKI is administered at an amount from about 5 mg to about 55 mg. In embodiments, the TKI is administered at an amount from about 5 mg to about 50 mg. In embodiments, the TKI is administered at an amount from about 5 mg to about 45 mg. In embodiments, the TKI is administered at an amount from about 5 mg to about 40 mg. In embodiments, the TKI is administered at an amount from about 5 mg to about 35 mg. In embodiments, the TKI is administered at an amount from about 5 mg to about 30 mg. In embodiments, the TKI is administered at an amount from about 5 mg to about 25 mg. In embodiments, the TKI is administered at an amount from about 5 mg to about 20 mg. In embodiments, the TKI is administered at an amount from about 5 mg to about 15 mg. In embodiments, the TKI is administered at an amount from about 5 mg to about 10 mg. In embodiments, the TKI is administered at an amount of about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, or 150 mg.

In embodiments, the TKI is administered at an amount from about 0.01 mg/kg to about 7.5 mg/kg. In embodiments, the TKI is administered at an amount from about 0.25 mg/kg to about 7.5 mg/kg. In embodiments, the TKI is administered at an amount from about 0.5 mg/kg to about 7.5 mg/kg. In embodiments, the TKI is administered at an amount from about 0.75 mg/kg to about 7.5 mg/kg. In embodiments, the TKI is administered at an amount from about 1 mg/kg to about 7.5 mg/kg. In embodiments, the TKI is administered at an amount from about 1.25 mg/kg to about 7.5 mg/kg. In embodiments, the TKI is administered at an amount from about 1.5 mg/kg to about 7.5 mg/kg. In embodiments, the TKI is administered at an amount from about 1.75 mg/kg to about 7.5 mg/kg. In embodiments, the TKI is administered at an amount from about 2 mg/kg to about 7.5 mg/kg. In embodiments, the TKI is administered at an amount from about 2.25 mg/kg to about 7.5 mg/kg. In embodiments, the TKI is administered at an amount from about 2.5 mg/kg to about 7.5 mg/kg. In embodiments, the TKI is administered at an amount from about 2.75 mg/kg to about 7.5 mg/kg. In embodiments, the TKI is administered at an amount from about 3 mg/kg to about 7.5 mg/kg. In embodiments, the TKI is administered at an amount from about 3.25 mg/kg to about 7.5 mg/kg. In embodiments, the TKI is administered at an amount from about 3.5 mg/kg to about 7.5 mg/kg. In embodiments, the TKI is administered at an amount from about 3.75 mg/kg to about 7.5 mg/kg. In embodiments, the TKI is administered at an amount from about 4 mg/kg to about 7.5 mg/kg. In embodiments, the TKI is administered at an amount from about 4.25 mg/kg to about 7.5 mg/kg. In embodiments, the TKI is administered at an amount from about 4.5 mg/kg to about 7.5 mg/kg. In embodiments, the TKI is administered at an amount from about 4.75 mg/kg to about 7.5 mg/kg. In embodiments, the TKI is administered at an amount from about 5 mg/kg to about 7.5 mg/kg. In embodiments, the TKI is administered at an amount from about 5.25 mg/kg to about 7.5 mg/kg. In embodiments, the TKI is administered at an amount from about 5.5 mg/kg to about 7.5 mg/kg. In embodiments, the TKI is administered at an amount from about 5.75 mg/kg to about 7.5 mg/kg. In embodiments, the TKI is administered at an amount from about 6 mg/kg to about 7.5 mg/kg. In embodiments, the TKI is administered at an amount from about 6.25 mg/kg to about 7.5 mg/kg. In embodiments, the TKI is administered at an amount from about 6.5 mg/kg to about 7.5 mg/kg. In embodiments, the TKI is administered at an amount from about 6.75 mg/kg to about 7.5 mg/kg. In embodiments, the TKI is administered at an amount from about 7 mg/kg to about 7.5 mg/kg. In embodiments, the TKI is administered at an amount from about 7.25 mg/kg to about 7.5 mg/kg.

In embodiments, the TKI is administered at an amount from about 0.01 mg/kg to about 7.25 mg/kg. In embodiments, the TKI is administered at an amount from about 0.01 mg/kg to about 7 mg/kg. In embodiments, the TKI is administered at an amount from about 0.01 mg/kg to about 6.75 mg/kg. In embodiments, the TKI is administered at an amount from about 0.01 mg/kg to about 6.5 mg/kg. In embodiments, the TKI is administered at an amount from about 0.01 mg/kg to about 6.25 mg/kg. In embodiments, the TKI is administered at an amount from about 0.01 mg/kg to about 6 mg/kg. In embodiments, the TKI is administered at an amount from about 0.01 mg/kg to about 5.75 mg/kg. In embodiments, the TKI is administered at an amount from about 0.01 mg/kg to about 5.5 mg/kg. In embodiments, the TKI is administered at an amount from about 0.01 mg/kg to about 5.25 mg/kg. In embodiments, the TKI is administered at an amount from about 0.01 mg/kg to about 5 mg/kg. In embodiments, the TKI is administered at an amount from about 0.01 mg/kg to about 4.75 mg/kg. In embodiments, the TKI is administered at an amount from about 0.01 mg/kg to about 4.5 mg/kg. In embodiments, the TKI is administered at an amount from about 0.01 mg/kg to about 4.25 mg/kg. In embodiments, the TKI is administered at an amount from about 0.01 mg/kg to about 4 mg/kg. In embodiments, the TKI is administered at an amount from about 0.01 mg/kg to about 3.75 mg/kg. In embodiments, the TKI is administered at an amount from about 0.01 mg/kg to about 3.5 mg/kg. In embodiments, the TKI is administered at an amount from about 0.01 mg/kg to about 3.25 mg/kg. In embodiments, the TKI is administered at an amount from about 0.01 mg/kg to about 3 mg/kg. In embodiments, the TKI is administered at an amount from about 0.01 mg/kg to about 2.75 mg/kg. In embodiments, the TKI is administered at an amount from about 0.01 mg/kg to about 2.5 mg/kg. In embodiments, the TKI is administered at an amount from about 0.01 mg/kg to about 2.25 mg/kg. In embodiments, the TKI is administered at an amount from about 0.01 mg/kg to about 2 mg/kg. In embodiments, the TKI is administered at an amount from about 0.01 mg/kg to about 1.75 mg/kg. In embodiments, the TKI is administered at an amount from about 0.01 mg/kg to about 1.5 mg/kg. In embodiments, the TKI is administered at an amount from about 0.01 mg/kg to about 1.25 mg/kg. In embodiments, the TKI is administered at an amount from about 0.01 mg/kg to about 1 mg/kg. In embodiments, the TKI is administered at an amount from about 0.01 mg/kg to about 0.75 mg/kg. In embodiments, the TKI is administered at an amount from about 0.01 mg/kg to about 0.5 mg/kg. In embodiments, the TKI is administered at an amount from about 0.01 mg/kg to about 0.25 mg/kg. In embodiments, the TKI is administered at an amount of about 0.01 mg/kg, 0.25 mg/kg, 0.5 mg/kg, 0.75 mg/kg, 1 mg/kg, 1.25 mg/kg, 1.5 mg/kg, 1.75 mg/kg, 2 mg/kg, 2.25 mg/kg, 2.5 mg/kg, 2.75 mg/kg, 3 mg/kg, 3.25 mg/kg, 3.5 mg/kg, 3.75 mg/kg, 4 mg/kg, 4.25 mg/kg, 4.5 mg/kg, 4.75 mg/kg, 5 mg/kg, 5.25 mg/kg, 5.5 mg/kg, 5.75 mg/kg, 6 mg/kg, 6.25 mg/kg, 6.5 mg/kg, 6.75 mg/kg, 7 mg/kg, 7.25 mg/kg, or 7.5 mg/kg.

In embodiments, the TKI is administered at an amount from about 0.01 mg/kg to about 4 mg/kg. In embodiments, the TKI is administered at an amount from about 0.2 mg/kg to about 4 mg/kg. In embodiments, the TKI is administered at an amount from about 0.4 mg/kg to about 4 mg/kg. In embodiments, the TKI is administered at an amount from about 0.8 mg/kg to about 4 mg/kg. In embodiments, the TKI is administered at an amount from about 1 mg/kg to about 4 mg/kg. In embodiments, the TKI is administered at an amount from about 1.2 mg/kg to about 4 mg/kg. In embodiments, the TKI is administered at an amount from about 1.4 mg/kg to about 4 mg/kg. In embodiments, the TKI is administered at an amount from about 1.8 mg/kg to about 4 mg/kg. In embodiments, the TKI is administered at an amount from about 2 mg/kg to about 4 mg/kg. In embodiments, the TKI is administered at an amount from about 2.2 mg/kg to about 4 mg/kg. In embodiments, the TKI is administered at an amount from about 2.4 mg/kg to about 4 mg/kg. In embodiments, the TKI is administered at an amount from about 2.8 mg/kg to about 4 mg/kg. In embodiments, the TKI is administered at an amount from about 3 mg/kg to about 4 mg/kg. In embodiments, the TKI is administered at an amount from about 3.2 mg/kg to about 4 mg/kg. In embodiments, the TKI is administered at an amount from about 3.4 mg/kg to about 4 mg/kg. In embodiments, the TKI is administered at an amount from about 3.8 mg/kg to about 4 mg/kg.

In embodiments, the TKI is administered at an amount from about 0.01 mg/kg to about 3.8 mg/kg. In embodiments, the TKI is administered at an amount from about 0.01 mg/kg to about 3.6 mg/kg. In embodiments, the TKI is administered at an amount from about 0.01 mg/kg to about 3.4 mg/kg. In embodiments, the TKI is administered at an amount from about 0.01 mg/kg to about 3.2 mg/kg. In embodiments, the TKI is administered at an amount from about 0.01 mg/kg to about 3 mg/kg. In embodiments, the TKI is administered at an amount from about 0.01 mg/kg to about 2.8 mg/kg. In embodiments, the TKI is administered at an amount from about 0.01 mg/kg to about 2.6 mg/kg. In embodiments, the TKI is administered at an amount from about 0.01 mg/kg to about 2.4 mg/kg. In embodiments, the TKI is administered at an amount from about 0.01 mg/kg to about 2.2 mg/kg. In embodiments, the TKI is administered at an amount from about 0.01 mg/kg to about 2 mg/kg. In embodiments, the TKI is administered at an amount from about 0.01 mg/kg to about 1.8 mg/kg. In embodiments, the TKI is administered at an amount from about 0.01 mg/kg to about 1.6 mg/kg. In embodiments, the TKI is administered at an amount from about 0.01 mg/kg to about 1.4 mg/kg. In embodiments, the TKI is administered at an amount from about 0.01 mg/kg to about 1.2 mg/kg. In embodiments, the TKI is administered at an amount from about 0.01 mg/kg to about 1 mg/kg. In embodiments, the TKI is administered at an amount from about 0.01 mg/kg to about 0.8 mg/kg. In embodiments, the TKI is administered at an amount from about 0.01 mg/kg to about 0.6 mg/kg. In embodiments, the TKI is administered at an amount from about 0.01 mg/kg to about 0.4 mg/kg. In embodiments, the TKI is administered at an amount from about 0.01 mg/kg to about 0.2 mg/kg. In embodiments, the TKI is administered at an amount of about 0.01 mg/kg, 0.2 mg/kg, 0.4 mg/kg, 0.6 mg/kg, 0.8 mg/kg, 1 mg/kg, 1.2 mg/kg, 1.4 mg/kg, 1.6 mg/kg, 1.8 mg/kg, 2 mg/kg, 2.2 mg/kg, 2.4 mg/kg, 2.6 mg/kg, 2.8 mg/kg, 3 mg/kg, 3.2 mg/kg, 3.4 mg/kg, 3.6 mg/kg, 3.8 mg/kg or 4 mg/kg.

In embodiments, triptolide or an analog thereof is administered at an amount from about 1 mg to about 300 mg. In embodiments, triptolide or an analog thereof is administered at an amount from about 5 mg to about 300 mg. In embodiments, triptolide or an analog thereof is administered at an amount from about 10 mg to about 300 mg. In embodiments, triptolide or an analog thereof is administered at an amount from about 15 mg to about 300 mg. In embodiments, triptolide or an analog thereof is administered at an amount from about 20 mg to about 300 mg. In embodiments, triptolide or an analog thereof is administered at an amount from about 25 mg to about 300 mg. In embodiments, triptolide or an analog thereof is administered at an amount from about 30 mg to about 300 mg. In embodiments, triptolide or an analog thereof is administered at an amount from about 35 mg to about 300 mg. In embodiments, triptolide or an analog thereof is administered at an amount from about 40 mg to about 300 mg. In embodiments, triptolide or an analog thereof is administered at an amount from about 45 mg to about 300 mg. In embodiments, triptolide or an analog thereof is administered at an amount from about 50 mg to about 300 mg. In embodiments, triptolide or an analog thereof is administered at an amount from about 55 mg to about 300 mg. In embodiments, triptolide or an analog thereof is administered at an amount from about 60 mg to about 300 mg. In embodiments, triptolide or an analog thereof is administered at an amount from about 65 mg to about 300 mg. In embodiments, triptolide or an analog thereof is administered at an amount from about 70 mg to about 300 mg. In embodiments, triptolide or an analog thereof is administered at an amount from about 75 mg to about 300 mg. In embodiments, triptolide or an analog thereof is administered at an amount from about 80 mg to about 300 mg. In embodiments, triptolide or an analog thereof is administered at an amount from about 85 mg to about 300 mg. In embodiments, triptolide or an analog thereof is administered at an amount from about 90 mg to about 300 mg. In embodiments, triptolide or an analog thereof is administered at an amount from about 95 mg to about 300 mg. In embodiments, triptolide or an analog thereof is administered at an amount from about 100 mg to about 300 mg. In embodiments, triptolide or an analog thereof is administered at an amount from about 105 mg to about 300 mg. In embodiments, triptolide or an analog thereof is administered at an amount from about 110 mg to about 300 mg. In embodiments, triptolide or an analog thereof is administered at an amount from about 115 mg to about 300 mg. In embodiments, triptolide or an analog thereof is administered at an amount from about 120 mg to about 300 mg. In embodiments, triptolide or an analog thereof is administered at an amount from about 125 mg to about 300 mg. In embodiments, triptolide or an analog thereof is administered at an amount from about 130 mg to about 300 mg. In embodiments, triptolide or an analog thereof is administered at an amount from about 135 mg to about 300 mg. In embodiments, triptolide or an analog thereof is administered at an amount from about 140 mg to about 300 mg. In embodiments, triptolide or an analog thereof is administered at an amount from about 145 mg to about 300 mg. In embodiments, triptolide or an analog thereof is administered at an amount from about 150 mg to about 300 mg. In embodiments, triptolide or an analog thereof is administered at an amount from about 155 mg to about 300 mg. In embodiments, triptolide or an analog thereof is administered at an amount from about 160 mg to about 300 mg. In embodiments, triptolide or an analog thereof is administered at an amount from about 165 mg to about 300 mg. In embodiments, triptolide or an analog thereof is administered at an amount from about 170 mg to about 300 mg. In embodiments, triptolide or an analog thereof is administered at an amount from about 175 mg to about 300 mg. In embodiments, triptolide or an analog thereof is administered at an amount from about 180 mg to about 300 mg. In embodiments, triptolide or an analog thereof is administered at an amount from about 185 mg to about 300 mg. In embodiments, triptolide or an analog thereof is administered at an amount from about 190 mg to about 300 mg. In embodiments, triptolide or an analog thereof is administered at an amount from about 195 mg to about 300 mg. In embodiments, triptolide or an analog thereof is administered at an amount from about 200 mg to about 300 mg. In embodiments, triptolide or an analog thereof is administered at an amount from about 205 mg to about 300 mg. In embodiments, triptolide or an analog thereof is administered at an amount from about 210 mg to about 300 mg. In embodiments, triptolide or an analog thereof is administered at an amount from about 215 mg to about 300 mg. In embodiments, triptolide or an analog thereof is administered at an amount from about 220 mg to about 300 mg. In embodiments, triptolide or an analog thereof is administered at an amount from about 225 mg to about 300 mg. In embodiments, triptolide or an analog thereof is administered at an amount from about 230 mg to about 300 mg. In embodiments, triptolide or an analog thereof is administered at an amount from about 235 mg to about 300 mg. In embodiments, triptolide or an analog thereof is administered at an amount from about 240 mg to about 300 mg. In embodiments, triptolide or an analog thereof is administered at an amount from about 245 mg to about 300 mg. In embodiments, triptolide or an analog thereof is administered at an amount from about 250 mg to about 300 mg. In embodiments, triptolide or an analog thereof is administered at an amount from about 255 mg to about 300 mg. In embodiments, triptolide or an analog thereof is administered at an amount from about 260 mg to about 300 mg. In embodiments, triptolide or an analog thereof is administered at an amount from about 265 mg to about 300 mg. In embodiments, triptolide or an analog thereof is administered at an amount from about 270 mg to about 300 mg. In embodiments, triptolide or an analog thereof is administered at an amount from about 275 mg to about 300 mg. In embodiments, triptolide or an analog thereof is administered at an amount from about 280 mg to about 300 mg. In embodiments, triptolide or an analog thereof is administered at an amount from about 285 mg to about 300 mg. In embodiments, triptolide or an analog thereof is administered at an amount from about 290 mg to about 300 mg. In embodiments, triptolide or an analog thereof is administered at an amount from about 295 mg to about 300 mg.

In embodiments, triptolide or an analog thereof is administered at an amount from about 1 mg to about 295 mg. In embodiments, triptolide or an analog thereof is administered at an amount from about 1 mg to about 290 mg. In embodiments, triptolide or an analog thereof is administered at an amount from about 1 mg to about 285 mg. In embodiments, triptolide or an analog thereof is administered at an amount from about 1 mg to about 280 mg. In embodiments, triptolide or an analog thereof is administered at an amount from about 1 mg to about 275 mg. In embodiments, triptolide or an analog thereof is administered at an amount from about 1 mg to about 270 mg. In embodiments, triptolide or an analog thereof is administered at an amount from about 5 mg to about 265 mg. In embodiments, triptolide or an analog thereof is administered at an amount from about 1 mg to about 260 mg. In embodiments, triptolide or an analog thereof is administered at an amount from about 1 mg to about 255 mg. In embodiments, triptolide or an analog thereof is administered at an amount from about 1 mg to about 250 mg. In embodiments, triptolide or an analog thereof is administered at an amount from about 1 mg to about 245 mg. In embodiments, triptolide or an analog thereof is administered at an amount from about 1 mg to about 240 mg. In embodiments, triptolide or an analog thereof is administered at an amount from about 1 mg to about 235 mg. In embodiments, triptolide or an analog thereof is administered at an amount from about 1 mg to about 230 mg. In embodiments, triptolide or an analog thereof is administered at an amount from about 1 mg to about 225 mg. In embodiments, triptolide or an analog thereof is administered at an amount from about 1 mg to about 220 mg. In embodiments, triptolide or an analog thereof is administered at an amount from about 1 mg to about 215 mg. In embodiments, triptolide or an analog thereof is administered at an amount from about 1 mg to about 210 mg. In embodiments, triptolide or an analog thereof is administered at an amount from about 1 mg to about 205 mg. In embodiments, triptolide or an analog thereof is administered at an amount from about 1 mg to about 200 mg. In embodiments, triptolide or an analog thereof is administered at an amount from about 1 mg to about 195 mg. In embodiments, triptolide or an analog thereof is administered at an amount from about 1 mg to about 190 mg. In embodiments, triptolide or an analog thereof is administered at an amount from about 1 mg to about 185 mg. In embodiments, triptolide or an analog thereof is administered at an amount from about 1 mg to about 180 mg. In embodiments, triptolide or an analog thereof is administered at an amount from about 1 mg to about 175 mg. In embodiments, triptolide or an analog thereof is administered at an amount from about 1 mg to about 170 mg. In embodiments, triptolide or an analog thereof is administered at an amount from about 1 mg to about 165 mg. In embodiments, triptolide or an analog thereof is administered at an amount from about 1 mg to about 160 mg. In embodiments, triptolide or an analog thereof is administered at an amount from about 1 mg to about 155 mg. In embodiments, triptolide or an analog thereof is administered at an amount from about 1 mg to about 150 mg. In embodiments, triptolide or an analog thereof is administered at an amount from about 1 mg to about 145 mg. In embodiments, triptolide or an analog thereof is administered at an amount from about 1 mg to about 140 mg. In embodiments, triptolide or an analog thereof is administered at an amount from about 1 mg to about 135 mg. In embodiments, triptolide or an analog thereof is administered at an amount from about 1 mg to about 130 mg. In embodiments, triptolide or an analog thereof is administered at an amount from about 1 mg to about 145 mg. In embodiments, triptolide or an analog thereof is administered at an amount from about 1 mg to about 140 mg. In embodiments, triptolide or an analog thereof is administered at an amount from about 1 mg to about 135 mg. In embodiments, triptolide or an analog thereof is administered at an amount from about 1 mg to about 130 mg. In embodiments, triptolide or an analog thereof is administered at an amount from about 1 mg to about 125 mg. In embodiments, triptolide or an analog thereof is administered at an amount from about 1 mg to about 120 mg. In embodiments, triptolide or an analog thereof is administered at an amount from about 1 mg to about 115 mg. In embodiments, triptolide or an analog thereof is administered at an amount from about 1 mg to about 110 mg. In embodiments, triptolide or an analog thereof is administered at an amount from about 1 mg to about 105 mg. In embodiments, triptolide or an analog thereof is administered at an amount from about 1 mg to about 100 mg. In embodiments, triptolide or an analog thereof is administered at an amount from about 1 mg to about 95 mg. In embodiments, triptolide or an analog thereof is administered at an amount from about 1 mg to about 90 mg. In embodiments, triptolide or an analog thereof is administered at an amount from about 1 mg to about 85 mg. In embodiments, triptolide or an analog thereof is administered at an amount from about 1 mg to about 80 mg. In embodiments, triptolide or an analog thereof is administered at an amount from about 1 mg to about 75 mg. In embodiments, triptolide or an analog thereof is administered at an amount from about 1 mg to about 70 mg. In embodiments, triptolide or an analog thereof is administered at an amount from about 1 mg to about 65 mg. In embodiments, triptolide or an analog thereof is administered at an amount from about 1 mg to about 60 mg. In embodiments, triptolide or an analog thereof is administered at an amount from about 1 mg to about 55 mg. In embodiments, triptolide or an analog thereof is administered at an amount from about 1 mg to about 50 mg. In embodiments, triptolide or an analog thereof is administered at an amount from about 1 mg to about 45 mg. In embodiments, triptolide or an analog thereof is administered at an amount from about 1 mg to about 40 mg. In embodiments, triptolide or an analog thereof is administered at an amount from about 1 mg to about 35 mg. In embodiments, triptolide or an analog thereof is administered at an amount from about 1 mg to about 30 mg. In embodiments, triptolide or an analog thereof is administered at an amount from about 1 mg to about 25 mg. In embodiments, triptolide or an analog thereof is administered at an amount from about 1 mg to about 20 mg. In embodiments, triptolide or an analog thereof is administered at an amount from about 1 mg to about 15 mg. In embodiments, triptolide or an analog thereof is administered at an amount from about 1 mg to about 10 mg. In embodiments, triptolide or an analog thereof is administered at an amount of about 1 mg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, 200 mg, 205 mg, 210 mg, 215 mg, 220 mg, 225 mg, 230 mg, 235 mg, 240 mg, 245 mg, 250 mg, 255 mg, 260 mg, 265 mg, 270 mg, 275 mg, 280 mg, 285 mg, 290 mg, 295 mg, or 300 mg.

In embodiments, triptolide or an analog thereof is administered at an amount from about 2 mg to about 106 mg. In embodiments, triptolide or an analog thereof is administered at an amount from about 6 mg to about 106 mg. In embodiments, triptolide or an analog thereof is administered at an amount from about 10 mg to about 106 mg. In embodiments, triptolide or an analog thereof is administered at an amount from about 14 mg to about 106 mg. In embodiments, triptolide or an analog thereof is administered at an amount from about 18 mg to about 106 mg. In embodiments, triptolide or an analog thereof is administered at an amount from about 22 mg to about 106 mg. In embodiments, triptolide or an analog thereof is administered at an amount from about 26 mg to about 106 mg. In embodiments, triptolide or an analog thereof is administered at an amount from about 30 mg to about 106 mg. In embodiments, triptolide or an analog thereof is administered at an amount from about 34 mg to about 106 mg. In embodiments, triptolide or an analog thereof is administered at an amount from about 38 mg to about 106 mg. In embodiments, triptolide or an analog thereof is administered at an amount from about 42 mg to about 106 mg. In embodiments, triptolide or an analog thereof is administered at an amount from about 46 mg to about 106 mg. In embodiments, triptolide or an analog thereof is administered at an amount from about 50 mg to about 106 mg. In embodiments, triptolide or an analog thereof is administered at an amount from about 54 mg to about 106 mg. In embodiments, triptolide or an analog thereof is administered at an amount from about 58 mg to about 106 mg. In embodiments, triptolide or an analog thereof is administered at an amount from about 62 mg to about 106 mg. In embodiments, triptolide or an analog thereof is administered at an amount from about 66 mg to about 106 mg. In embodiments, triptolide or an analog thereof is administered at an amount from about 70 mg to about 106 mg. In embodiments, triptolide or an analog thereof is administered at an amount from about 74 mg to about 106 mg. In embodiments, triptolide or an analog thereof is administered at an amount from about 78 mg to about 106 mg. In embodiments, triptolide or an analog thereof is administered at an amount from about 82 mg to about 106 mg. In embodiments, triptolide or an analog thereof is administered at an amount from about 86 mg to about 106 mg. In embodiments, triptolide or an analog thereof is administered at an amount from about 90 mg to about 106 mg. In embodiments, triptolide or an analog thereof is administered at an amount from about 94 mg to about 106 mg. In embodiments, triptolide or an analog thereof is administered at an amount from about 98 mg to about 106 mg. In embodiments, triptolide or an analog thereof is administered at an amount from about 102 mg to about 106 mg.

In embodiments, triptolide or an analog thereof is administered at an amount from about 2 mg to about 102 mg. In embodiments, triptolide or an analog thereof is administered at an amount from about 2 mg to about 98 mg. In embodiments, triptolide or an analog thereof is administered at an amount from about 2 mg to about 94 mg. In embodiments, triptolide or an analog thereof is administered at an amount from about 2 mg to about 90 mg. In embodiments, triptolide or an analog thereof is administered at an amount from about 2 mg to about 86 mg. In embodiments, triptolide or an analog thereof is administered at an amount from about 2 mg to about 82 mg. In embodiments, triptolide or an analog thereof is administered at an amount from about 2 mg to about 78 mg. In embodiments, triptolide or an analog thereof is administered at an amount from about 2 mg to about 74 mg. In embodiments, triptolide or an analog thereof is administered at an amount from about 2 mg to about 70 mg. In embodiments, triptolide or an analog thereof is administered at an amount from about 2 mg to about 66 mg. In embodiments, triptolide or an analog thereof is administered at an amount from about 2 mg to about 62 mg. In embodiments, triptolide or an analog thereof is administered at an amount from about 2 mg to about 58 mg. In embodiments, triptolide or an analog thereof is administered at an amount from about 2 mg to about 54 mg. In embodiments, triptolide or an analog thereof is administered at an amount from about 2 mg to about 50 mg. In embodiments, triptolide or an analog thereof is administered at an amount from about 2 mg to about 46 mg. In embodiments, triptolide or an analog thereof is administered at an amount from about 2 mg to about 42 mg. In embodiments, triptolide or an analog thereof is administered at an amount from about 2 mg to about 38 mg. In embodiments, triptolide or an analog thereof is administered at an amount from about 2 mg to about 34 mg. In embodiments, triptolide or an analog thereof is administered at an amount from about 2 mg to about 30 mg. In embodiments, triptolide or an analog thereof is administered at an amount from about 2 mg to about 26 mg. In embodiments, triptolide or an analog thereof is administered at an amount from about 2 mg to about 22 mg. In embodiments, triptolide or an analog thereof is administered at an amount from about 2 mg to about 18 mg. In embodiments, triptolide or an analog thereof is administered at an amount from about 2 mg to about 14 mg. In embodiments, triptolide or an analog thereof is administered at an amount from about 2 mg to about 10 mg. In embodiments, triptolide or an analog thereof is administered at an amount from about 2 mg to about 6 mg. In embodiments, triptolide or an analog thereof is administered at an amount of about 2 mg, 6 mg, 10 mg, 14 mg, 18 mg, 22 mg, 26 mg, 30 mg, 34 mg, 38 mg, 42 mg, 46 mg, 50 mg, 54 mg, 58 mg, 62 mg, 66 mg, 70 mg, 74 mg, 80 mg, 84 mg, 88 mg, 92 mg, 96 mg, 100 mg, or 106 mg.

In embodiments, triptolide or an analog thereof is administered at an amount from about 0.01 mg/kg to about 6 mg/kg. In embodiments, triptolide or an analog thereof is administered at an amount from about 0.1 mg/kg to about 6 mg/kg. In embodiments, triptolide or an analog thereof is administered at an amount from about 0.2 mg/kg to about 6 mg/kg. In embodiments, triptolide or an analog thereof is administered at an amount from about 0.3 mg/kg to about 6 mg/kg. In embodiments, triptolide or an analog thereof is administered at an amount from about 0.4 mg/kg to about 6 mg/kg. In embodiments, triptolide or an analog thereof is administered at an amount from about 0.5 mg/kg to about 6 mg/kg. In embodiments, triptolide or an analog thereof is administered at an amount from about 0.6 mg/kg to about 6 mg/kg. In embodiments, triptolide or an analog thereof is administered at an amount from about 0.7 mg/kg to about 6 mg/kg. In embodiments, triptolide or an analog thereof is administered at an amount from about 0.8 mg/kg to about 6 mg/kg. In embodiments, triptolide or an analog thereof is administered at an amount from about 0.9 mg/kg to about 6 mg/kg. In embodiments, triptolide or an analog thereof is administered at an amount from about 1 mg/kg to about 6 mg/kg. In embodiments, triptolide or an analog thereof is administered at an amount from about 1.1 mg/kg to about 6 mg/kg. In embodiments, triptolide or an analog thereof is administered at an amount from about 1.2 mg/kg to about 6 mg/kg. In embodiments, triptolide or an analog thereof is administered at an amount from about 1.3 mg/kg to about 6 mg/kg. In embodiments, triptolide or an analog thereof is administered at an amount from about 1.4 mg/kg to about 6 mg/kg. In embodiments, triptolide or an analog thereof is administered at an amount from about 1.5 mg/kg to about 6 mg/kg. In embodiments, triptolide or an analog thereof is administered at an amount from about 1.6 mg/kg to about 6 mg/kg. In embodiments, triptolide or an analog thereof is administered at an amount from about 1.7 mg/kg to about 6 mg/kg. In embodiments, triptolide or an analog thereof is administered at an amount from about 1.8 mg/kg to about 6 mg/kg. In embodiments, triptolide or an analog thereof is administered at an amount from about 1.9 mg/kg to about 6 mg/kg. In embodiments, triptolide or an analog thereof is administered at an amount from about 2 mg/kg to about 6 mg/kg. In embodiments, triptolide or an analog thereof is administered at an amount from about 2.1 mg/kg to about 6 mg/kg. In embodiments, triptolide or an analog thereof is administered at an amount from about 2.2 mg/kg to about 6 mg/kg. In embodiments, triptolide or an analog thereof is administered at an amount from about 2.3 mg/kg to about 6 mg/kg. In embodiments, triptolide or an analog thereof is administered at an amount from about 2.4 mg/kg to about 6 mg/kg. In embodiments, triptolide or an analog thereof is administered at an amount from about 2.5 mg/kg to about 6 mg/kg. In embodiments, triptolide or an analog thereof is administered at an amount from about 2.6 mg/kg to about 6 mg/kg. In embodiments, triptolide or an analog thereof is administered at an amount from about 2.7 mg/kg to about 6 mg/kg. In embodiments, triptolide or an analog thereof is administered at an amount from about 2.8 mg/kg to about 6 mg/kg. In embodiments, triptolide or an analog thereof is administered at an amount from about 2.9 mg/kg to about 6 mg/kg. In embodiments, triptolide or an analog thereof is administered at an amount from about 3 mg/kg to about 6 mg/kg. In embodiments, triptolide or an analog thereof is administered at an amount from about 3.1 mg/kg to about 6 mg/kg. In embodiments, triptolide or an analog thereof is administered at an amount from about 3.2 mg/kg to about 6 mg/kg. In embodiments, triptolide or an analog thereof is administered at an amount from about 3.3 mg/kg to about 6 mg/kg. In embodiments, triptolide or an analog thereof is administered at an amount from about 3.4 mg/kg to about 6 mg/kg. In embodiments, triptolide or an analog thereof is administered at an amount from about 3.5 mg/kg to about 6 mg/kg. In embodiments, triptolide or an analog thereof is administered at an amount from about 3.6 mg/kg to about 6 mg/kg. In embodiments, triptolide or an analog thereof is administered at an amount from about 3.7 mg/kg to about 6 mg/kg. In embodiments, triptolide or an analog thereof is administered at an amount from about 3.8 mg/kg to about 6 mg/kg. In embodiments, triptolide or an analog thereof is administered at an amount from about 3.9 mg/kg to about 6 mg/kg. In embodiments, triptolide or an analog thereof is administered at an amount from about 4 mg/kg to about 6 mg/kg. In embodiments, triptolide or an analog thereof is administered at an amount from about 4.1 mg/kg to about 6 mg/kg. In embodiments, triptolide or an analog thereof is administered at an amount from about 4.2 mg/kg to about 6 mg/kg. In embodiments, triptolide or an analog thereof is administered at an amount from about 4.3 mg/kg to about 6 mg/kg. In embodiments, triptolide or an analog thereof is administered at an amount from about 4.4 mg/kg to about 6 mg/kg. In embodiments, triptolide or an analog thereof is administered at an amount from about 4.5 mg/kg to about 6 mg/kg. In embodiments, triptolide or an analog thereof is administered at an amount from about 4.6 mg/kg to about 6 mg/kg. In embodiments, triptolide or an analog thereof is administered at an amount from about 4.7 mg/kg to about 6 mg/kg. In embodiments, triptolide or an analog thereof is administered at an amount from about 4.8 mg/kg to about 6 mg/kg. In embodiments, triptolide or an analog thereof is administered at an amount from about 4.9 mg/kg to about 6 mg/kg. In embodiments, triptolide or an analog thereof is administered at an amount from about 5 mg/kg to about 6 mg/kg. In embodiments, triptolide or an analog thereof is administered at an amount from about 5.1 mg/kg to about 6 mg/kg. In embodiments, triptolide or an analog thereof is administered at an amount from about 5.2 mg/kg to about 6 mg/kg. In embodiments, triptolide or an analog thereof is administered at an amount from about 5.3 mg/kg to about 6 mg/kg. In embodiments, triptolide or an analog thereof is administered at an amount from about 5.4 mg/kg to about 6 mg/kg. In embodiments, triptolide or an analog thereof is administered at an amount from about 5.5 mg/kg to about 6 mg/kg. In embodiments, triptolide or an analog thereof is administered at an amount from about 5.6 mg/kg to about 6 mg/kg. In embodiments, triptolide or an analog thereof is administered at an amount from about 5.7 mg/kg to about 6 mg/kg. In embodiments, triptolide or an analog thereof is administered at an amount from about 5.8 mg/kg to about 6 mg/kg. In embodiments, triptolide or an analog thereof is administered at an amount from about 5.9 mg/kg to about 6 mg/kg.

In embodiments, triptolide or an analog thereof is administered at an amount from about 0.01 mg/kg to about 5.9 mg/kg. In embodiments, triptolide or an analog thereof is administered at an amount from about 0.01 mg/kg to about 5.8 mg/kg. In embodiments, triptolide or an analog thereof is administered at an amount from about 0.01 mg/kg to about 5.7 mg/kg. In embodiments, triptolide or an analog thereof is administered at an amount from about 0.01 mg/kg to about 5.6 mg/kg. In embodiments, triptolide or an analog thereof is administered at an amount from about 0.01 mg/kg to about 5.5 mg/kg. In embodiments, triptolide or an analog thereof is administered at an amount from about 0.01 mg/kg to about 5.4 mg/kg. In embodiments, triptolide or an analog thereof is administered at an amount from about 0.01 mg/kg to about 5.3 mg/kg. In embodiments, triptolide or an analog thereof is administered at an amount from about 0.01 mg/kg to about 5.2 mg/kg. In embodiments, triptolide or an analog thereof is administered at an amount from about 0.01 mg/kg to about 5.1 mg/kg. In embodiments, triptolide or an analog thereof is administered at an amount from about 0.01 mg/kg to about 5 mg/kg. In embodiments, triptolide or an analog thereof is administered at an amount from about 0.01 mg/kg to about 4.9 mg/kg. In embodiments, triptolide or an analog thereof is administered at an amount from about 0.01 mg/kg to about 4.8 mg/kg. In embodiments, triptolide or an analog thereof is administered at an amount from about 0.01 mg/kg to about 4.7 mg/kg. In embodiments, triptolide or an analog thereof is administered at an amount from about 0.01 mg/kg to about 4.6 mg/kg. In embodiments, triptolide or an analog thereof is administered at an amount from about 0.01 mg/kg to about 4.5 mg/kg. In embodiments, triptolide or an analog thereof is administered at an amount from about 0.01 mg/kg to about 4.4 mg/kg. In embodiments, triptolide or an analog thereof is administered at an amount from about 0.01 mg/kg to about 4.3 mg/kg. In embodiments, triptolide or an analog thereof is administered at an amount from about 0.01 mg/kg to about 4.2 mg/kg. In embodiments, triptolide or an analog thereof is administered at an amount from about 0.01 mg/kg to about 4.1 mg/kg. In embodiments, triptolide or an analog thereof is administered at an amount from about 0.01 mg/kg to about 4 mg/kg. In embodiments, triptolide or an analog thereof is administered at an amount from about 0.01 mg/kg to about 3.9 mg/kg. In embodiments, triptolide or an analog thereof is administered at an amount from about 0.01 mg/kg to about 3.8 mg/kg. In embodiments, triptolide or an analog thereof is administered at an amount from about 0.01 mg/kg to about 3.7 mg/kg. In embodiments, triptolide or an analog thereof is administered at an amount from about 0.01 mg/kg to about 3.6 mg/kg. In embodiments, triptolide or an analog thereof is administered at an amount from about 0.01 mg/kg to about 3.5 mg/kg. In embodiments, triptolide or an analog thereof is administered at an amount from about 0.01 mg/kg to about 3.4 mg/kg. In embodiments, triptolide or an analog thereof is administered at an amount from about 0.01 mg/kg to about 3.3 mg/kg. In embodiments, triptolide or an analog thereof is administered at an amount from about 0.01 mg/kg to about 3.2 mg/kg. In embodiments, triptolide or an analog thereof is administered at an amount from about 0.01 mg/kg to about 3.1 mg/kg. In embodiments, triptolide or an analog thereof is administered at an amount from about 0.01 mg/kg to about 3 mg/kg. In embodiments, triptolide or an analog thereof is administered at an amount from about 0.01 mg/kg to about 2.9 mg/kg. In embodiments, triptolide or an analog thereof is administered at an amount from about 0.01 mg/kg to about 2.8 mg/kg. In embodiments, triptolide or an analog thereof is administered at an amount from about 0.01 mg/kg to about 2.7 mg/kg. In embodiments, triptolide or an analog thereof is administered at an amount from about 0.01 mg/kg to about 2.6 mg/kg. In embodiments, triptolide or an analog thereof is administered at an amount from about 0.01 mg/kg to about 2.5 mg/kg. In embodiments, triptolide or an analog thereof is administered at an amount from about 0.01 mg/kg to about 2.4 mg/kg. In embodiments, triptolide or an analog thereof is administered at an amount from about 0.01 mg/kg to about 2.3 mg/kg. In embodiments, triptolide or an analog thereof is administered at an amount from about 0.01 mg/kg to about 2.2 mg/kg. In embodiments, triptolide or an analog thereof is administered at an amount from about 0.01 mg/kg to about 2.1 mg/kg. In embodiments, triptolide or an analog thereof is administered at an amount from about 0.01 mg/kg to about 2 mg/kg. In embodiments, triptolide or an analog thereof is administered at an amount from about 0.01 mg/kg to about 1.9 mg/kg. In embodiments, triptolide or an analog thereof is administered at an amount from about 0.01 mg/kg to about 1.8 mg/kg. In embodiments, triptolide or an analog thereof is administered at an amount from about 0.01 mg/kg to about 1.7 mg/kg. In embodiments, triptolide or an analog thereof is administered at an amount from about 0.01 mg/kg to about 1.6 mg/kg. In embodiments, triptolide or an analog thereof is administered at an amount from about 0.01 mg/kg to about 1.5 mg/kg. In embodiments, triptolide or an analog thereof is administered at an amount from about 0.01 mg/kg to about 1.4 mg/kg. In embodiments, triptolide or an analog thereof is administered at an amount from about 0.01 mg/kg to about 1.3 mg/kg. In embodiments, triptolide or an analog thereof is administered at an amount from about 0.01 mg/kg to about 1.2 mg/kg. In embodiments, triptolide or an analog thereof is administered at an amount from about 0.01 mg/kg to about 1.1 mg/kg. In embodiments, triptolide or an analog thereof is administered at an amount from about 0.01 mg/kg to about 1 mg/kg. In embodiments, triptolide or an analog thereof is administered at an amount from about 0.01 mg/kg to about 0.9 mg/kg. In embodiments, triptolide or an analog thereof is administered at an amount from about 0.01 mg/kg to about 0.8 mg/kg. In embodiments, triptolide or an analog thereof is administered at an amount from about 0.01 mg/kg to about 0.7 mg/kg. In embodiments, triptolide or an analog thereof is administered at an amount from about 0.01 mg/kg to about 0.6 mg/kg. In embodiments, triptolide or an analog thereof is administered at an amount from about 0.01 mg/kg to about 0.5 mg/kg. In embodiments, triptolide or an analog thereof is administered at an amount from about 0.01 mg/kg to about 0.4 mg/kg. In embodiments, triptolide or an analog thereof is administered at an amount from about 0.01 mg/kg to about 0.3 mg/kg. In embodiments, triptolide or an analog thereof is administered at an amount from about 0.01 mg/kg to about 0.2 mg/kg. In embodiments, triptolide or an analog thereof is administered at an amount from about 0.01 mg/kg to about 0.1 mg/kg. In embodiments, triptolide or an analog thereof is administered at an amount of about 0.01 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, or 6 mg/kg.

In embodiments, triptolide or an analog thereof is administered at an amount from about 0.01 mg/kg to about 2.5 mg/kg. In embodiments, triptolide or an analog thereof is administered at an amount from about 0.1 mg/kg to about 2.5 mg/kg. In embodiments, triptolide or an analog thereof is administered at an amount from about 0.2 mg/kg to about 2.5 mg/kg. In embodiments, triptolide or an analog thereof is administered at an amount from about 0.3 mg/kg to about 2.5 mg/kg. In embodiments, triptolide or an analog thereof is administered at an amount from about 0.4 mg/kg to about 2.5 mg/kg. In embodiments, triptolide or an analog thereof is administered at an amount from about 0.5 mg/kg to about 2.5 mg/kg. In embodiments, triptolide or an analog thereof is administered at an amount from about 0.6 mg/kg to about 2.5 mg/kg. In embodiments, triptolide or an analog thereof is administered at an amount from about 0.7 mg/kg to about 2.5 mg/kg. In embodiments, triptolide or an analog thereof is administered at an amount from about 0.8 mg/kg to about 2.5 mg/kg. In embodiments, triptolide or an analog thereof is administered at an amount from about 0.9 mg/kg to about 2.5 mg/kg. In embodiments, triptolide or an analog thereof is administered at an amount from about 1 mg/kg to about 2.5 mg/kg. In embodiments, triptolide or an analog thereof is administered at an amount from about 1.1 mg/kg to about 2.5 mg/kg. In embodiments, triptolide or an analog thereof is administered at an amount from about 1.2 mg/kg to about 2.5 mg/kg. In embodiments, triptolide or an analog thereof is administered at an amount from about 1.3 mg/kg to about 2.5 mg/kg. In embodiments, triptolide or an analog thereof is administered at an amount from about 1.4 mg/kg to about 2.5 mg/kg. In embodiments, triptolide or an analog thereof is administered at an amount from about 1.5 mg/kg to about 2.5 mg/kg. In embodiments, triptolide or an analog thereof is administered at an amount from about 1.6 mg/kg to about 2.5 mg/kg. In embodiments, triptolide or an analog thereof is administered at an amount from about 1.7 mg/kg to about 2.5 mg/kg. In embodiments, triptolide or an analog thereof is administered at an amount from about 1.8 mg/kg to about 2.5 mg/kg. In embodiments, triptolide or an analog thereof is administered at an amount from about 1.9 mg/kg to about 2.5 mg/kg. In embodiments, triptolide or an analog thereof is administered at an amount from about 2 mg/kg to about 2.5 mg/kg. In embodiments, triptolide or an analog thereof is administered at an amount from about 2.1 mg/kg to about 2.5 mg/kg. In embodiments, triptolide or an analog thereof is administered at an amount from about 2.2 mg/kg to about 2.5 mg/kg. In embodiments, triptolide or an analog thereof is administered at an amount from about 2.3 mg/kg to about 2.5 mg/kg. In embodiments, triptolide or an analog thereof is administered at an amount from about 2.4 mg/kg to about 2.5 mg/kg.

In embodiments, triptolide or an analog thereof is administered at an amount from about 0.01 mg/kg to about 2.4 mg/kg. In embodiments, triptolide or an analog thereof is administered at an amount from about 0.01 mg/kg to about 2.3 mg/kg. In embodiments, triptolide or an analog thereof is administered at an amount from about 0.01 mg/kg to about 2.2 mg/kg. In embodiments, triptolide or an analog thereof is administered at an amount from about 0.01 mg/kg to about 2.1 mg/kg. In embodiments, triptolide or an analog thereof is administered at an amount from about 0.01 mg/kg to about 2 mg/kg. In embodiments, triptolide or an analog thereof is administered at an amount from about 0.01 mg/kg to about 1.9 mg/kg. In embodiments, triptolide or an analog thereof is administered at an amount from about 0.01 mg/kg to about 1.8 mg/kg. In embodiments, triptolide or an analog thereof is administered at an amount from about 0.01 mg/kg to about 1.7 mg/kg. In embodiments, triptolide or an analog thereof is administered at an amount from about 0.01 mg/kg to about 1.6 mg/kg. In embodiments, triptolide or an analog thereof is administered at an amount from about 0.01 mg/kg to about 1.5 mg/kg. In embodiments, triptolide or an analog thereof is administered at an amount from about 0.01 mg/kg to about 1.4 mg/kg. In embodiments, triptolide or an analog thereof is administered at an amount from about 0.01 mg/kg to about 1.3 mg/kg. In embodiments, triptolide or an analog thereof is administered at an amount from about 0.01 mg/kg to about 1.2 mg/kg. In embodiments, triptolide or an analog thereof is administered at an amount from about 0.01 mg/kg to about 1 mg/kg. In embodiments, triptolide or an analog thereof is administered at an amount from about 0.01 mg/kg to about 0.9 mg/kg. In embodiments, triptolide or an analog thereof is administered at an amount from about 0.01 mg/kg to about 0.8 mg/kg. In embodiments, triptolide or an analog thereof is administered at an amount from about 0.01 mg/kg to about 0.7 mg/kg. In embodiments, triptolide or an analog thereof is administered at an amount from about 0.01 mg/kg to about 0.6 mg/kg. In embodiments, triptolide or an analog thereof is administered at an amount from about 0.01 mg/kg to about 0.5 mg/kg. In embodiments, triptolide or an analog thereof is administered at an amount from about 0.01 mg/kg to about 0.4 mg/kg. In embodiments, triptolide or an analog thereof is administered at an amount from about 0.01 mg/kg to about 0.3 mg/kg. In embodiments, triptolide or an analog thereof is administered at an amount from about 0.01 mg/kg to about 0.2 mg/kg. In embodiments, triptolide or an analog thereof is administered at an amount from about 0.01 mg/kg to about 0.1 mg/kg. In embodiments, triptolide or an analog thereof is administered at an amount of about 0.01 mg/kg, 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, or 2.5 mg/kg.

Methods of Preventing Resistance

Applicant has discovered that administration of triptolide or an analog thereof can prevent resistance of cancer cells to tyrosine kinase inhibitors for the treatment of cancer. Applicant has found that, surprisingly, triptolide and its analogs can when administered alone or in combination (e.g. simultaneous or sequential administration) with a TKI (e.g. Osimertinib, etc.) can inhibit cancer cell resistance to the TKI. Further, Applicant has shown that administration of triptolide or its analogs can re-sensitize cancer cells that previously developed resistance to TKIs. Thus, in an aspect is provided a method of preventing resistance to a tyrosine kinase inhibitor (TKI) in a subject having cancer, the method including administering to the subject triptolide or an analog thereof.

As used herein, the term "resistance" refers to lack of sensitivity or intended response of a cancer cell or cancer to a therapeutic agent, for example a chemotherapeutic or an anti-cancer agent. For example, resistance to a TKI can refer to loss of the anti-cancer effects (e.g. reduction in tumor volume or tumor volume growth) of the TKI. In embodiments, resistance is resistance to a chemotherapeutic. Thus, a "chemotherapeutic resistant cancer" is a cancer that lacks sensitivity or the intended response to a chemotherapeutic. In embodiments, resistance is resistance to an anti-cancer agent. In embodiments, the anti-cancer agent is a TKI. For example, a cancer cell may develop resistance to EGFR TKI treatment due to a mutation (e.g. T790M, E746-A750 deletion, etc.) that arises in the EGFR gene.

The term "sensitive" or "sensitivity" is used herein to refer to the intended response of a cell or population of cells to a therapeutic agent. In embodiments, the cell or population of cells may be cancer cell(s). In embodiments, the therapeutic agent may be an anti-cancer agent (e.g. a TKI) or a chemotherapeutic. Sensitivity may be measured as growth arrest, quiescence, senescence, apoptosis, or other forms of programmed cell death in response to the therapeutic agent; for example, cell apoptosis in response to a cytotoxic agent. Sensitivity to a therapeutic agent may be measured as inhibition or modulation of tumor growth. Thus, preventing resistance can refer to maintaining sensitivity to a therapeutic agent (e.g. a TKI). Preventing resistance can refer to reversing resistance, thereby reverting to prior sensitivity of the response before development of resistance (e.g. 20%, 30%, 40%, 50%, 60%, 79%, 80%, 90%, or 100% of the intended response prior to development of resistance).

For the method provided herein, in embodiments, the triptolide analog is minnelide, (5R)-5 hydroxy triptolide, 14b-fluoro triptolide, MRx102 or PG490-88. In embodiments, the triptolide analog is minnelide.

In embodiments, the TKI is an epithelial growth factor receptor (EGFR) TKI, an anaplastic lymphoma kinase (ALK) TKI, a ROS proto-oncogene 1 (ROS1) TKI, a platelet derived growth factor receptor (PDGFR) TKI, a vascular endothelial growth factor receptor (VEGFR) TKI, an insulin receptor (InsR) TKI, a Src TKI, a c-Kit TKI, a fibroblast growth factor receptor (FGFR) TKI, a human epidermal growth factor receptor 2 (HER2) TKI, a B-Raf proto-oncogene (BRAF) TKI, a mitogen-activated protein kinase (MAPK) TKI, a neurotrophin tyrosine kinase receptor (NTRK) TKI, a RET proto-oncogene (RET) TKI, a mesenchymal-epithelial transition factor receptor (MET) TKI, or an Abl TKI. For the method provided herein, in embodiments, the TKI is an EGFR TKI. In embodiments, the EGFR TKI is Osimertinib (Tagrisso), Erlotinib (Tarceva), Gefitinib, or Afatinib. In embodiments, the EGFR TKI is Osimertinib.

In embodiments, the method further includes administering to the subject the tyrosine kinase inhibitor. In embodiments, the TKI and triptolide or analog thereof are administered sequentially. In embodiments, the TKI and triptolide or analog thereof are administered simultaneously.

In embodiments, the cancer is breast cancer, colon cancer, lung cancer, leukemia, thyroid cancer, liver cancer, melanoma, skin cancer, kidney cancer, bladder cancer or head and neck cancer. In embodiments, the cancer is lung cancer. In embodiments, the lung cancer is non-small lung cell carcinoma. In embodiments, the cancer is a chemotherapeutic resistant cancer. In embodiments, the subject has been previously treated for the cancer.

Pharmaceutical Compositions

In embodiments, the pharmaceutical compositions provided herein are contemplated to be effective for treating cancer in a subject in need thereof. In embodiments, the cancer is resistant, has developed resistance, has decreased sensitivity, or is at risk of developing resistance or decreased sensitivity (e.g. due to acquired mutations, for example in the EGFR gene) to tyrosine kinase inhibitors (TKI). The pharmaceutical compositions are further contemplated to be effective for preventing resistance and/or increasing sensitivity to a TKI in a subject having cancer. Thus, in an aspect is provided a pharmaceutical composition including a tyrosine kinase inhibitor (TKI), triptolide or analog thereof, and a pharmaceutically acceptable excipient.

In embodiments, the pharmaceutical composition includes a tyrosine kinase inhibitor (TKI), triptolide, and a pharmaceutically acceptable excipient. In embodiments, the pharmaceutical composition does not include administration of any anti-cancer agent other than the recited agents (e.g. a TKI and/or triptolide (or analog thereof)). In embodiments, the pharmaceutical composition does not include administration of any active pharmaceutical agent other than the recited agents (e.g. a TKI and/or triptolide (or analog thereof)). In embodiments, the pharmaceutical composition includes a tyrosine kinase inhibitor (TKI), a triptolide analog, and a pharmaceutically acceptable excipient. In embodiments, the tyrosine kinase inhibitor is an epithelial growth factor receptor (EGFR) TKI, a platelet derived growth factor receptor (PDGFR) TKI, a vascular endothelial growth factor receptor (VEGFR) TKI, an insulin receptor (InsR) TKI, a Src TKI, a c-Kit TKI, or an Abl TKI. In embodiments, the tyrosine kinase inhibitor is an EGFR TKI. In embodiments, the tyrosine kinase inhibitor is a PDGFR TKI. In embodiments, the tyrosine kinase inhibitor is a VEGFR TKI. In embodiments, the tyrosine kinase inhibitor is an InsR TKI. In embodiments, the tyrosine kinase inhibitor is a c-Kit TKI. In embodiments, the tyrosine kinase inhibitor is a Src TKI. In embodiments, the tyrosine kinase inhibitor is a Abl TKI.

In embodiments, the TKI is acalabrutinib (Calquence). In embodiments, the TKI is afatinib (Gilotrif). In embodiments, the TKI is alectinib (Alecensa). In embodiments, the TKI is avapritinib. In embodiments, the TKI is axitinib (Inlyta). In embodiments, the TKI is bosutinib (Bosulif). In embodiments, the TKI is cabozantinib (Cabometyx, Cometriq). In embodiments, the TKI is crizotinib (Xalkori). In embodiments, the TKI is dacomitinib (Vizimpro). In embodiments, the TKI is dasatinib (Sprycel) In embodiments, the TKI is entrectinib (Rozlytrek). In embodiments, the TKI is erlotinib (Tarceva). In embodiments, the TKI is gilteritinib (Xospata). In embodiments, the TKI is ibrutinib (Imbruvica). In embodiments, the TKI is imatinib (Glivec). In embodiments, the TKI is lapatinib (Tykerb). In embodiments, the TKI is midostaurin (Rydapt). In embodiments, the TKI is neratinib (Nerlynx). In embodiments, the TKI is nilotinib (Tasigna). In embodiments, the TKI is pacritinib. In embodiments, the TKI is pazopanib (Votrient) In embodiments, the TKI is pexidartinib (Turalio). In embodiments, the TKI is ponatinib (Iclusig). In embodiments, the TKI is quizartinib. In embodiments, the TKI is regorafenib (Stivarga). In embodiments, the TKI is sorafenib (Nexavar). In embodiments, the TKI is sunitinib (Sutent). In embodiments, the TKI is vandetanib (Caprelsa). In embodiments, the TKI is vemurafenib. In embodiments, the TKI is zanubrutinib (Brukinsa). In embodiments, the TKI is ziv-aflibercept (Zaltrap). In embodiments, the TKI is a salt of a TKI provided herein. In embodiments, the compositions include more than one TKI with triptolide or an analog thereof.

For the pharmaceutical compositions provided herein, in embodiments the EGFR TKI is osimertinib (Tagrisso), erlotinib (Tarceva), gefitinib, or afatinib. In embodiments, the EGFR TKI is osimertinib. In embodiments, the EGFR TKI is erlotinib. In embodiments, the EGFR TKI is gefitinib. In embodiments, the EGFR TKI is afatinib.

For the pharmaceutical compositions provided herein, in embodiments the PDGFR TKI is nilotinib, imatinib, or sunitinib. In embodiments, the PDGFR TKI is nilotinib. In embodiments, the PDGFR TKI is imatinib. In embodiments, the PDGFR TKI is sunitinib.

For the pharmaceutical compositions provided herein, in embodiments the VEGFR TKI is pazopanib, sorafenib, ponatinib, sunitinib, or axitinib. In embodiments, the VEGFR TKI is pazopanib. In embodiments, the VEGFR TKI is sorafenib. In embodiments, the VEGFR TKI is ponatinib. In embodiments, the VEGFR TKI is sunitinib. In embodiments, the VEGFR TKI is axitinib.

For the pharmaceutical compositions provided herein, in embodiments the Src TKI is nilotinib, imatinib, sunitinib, bosutinib, saracatinib, or dasatinib. In embodiments, the Src TKI is nilotinib. In embodiments, the Src TKI is imatinib. In embodiments, the Src TKI is sunitinib. In embodiments, the Src TKI is bosutinib. In embodiments, the Src TKI is saracatinib. In embodiments, the Src TKI is dasatinib.

For the pharmaceutical compositions provided herein, in embodiments the Abl TKI is dasatinib, bosutinib, ponatinib, or bafetinib. In embodiments, the Abl TKI is dasatinib. In embodiments, the Abl TKI is bosutinib. In embodiments, the Abl TKI is ponatinib. In embodiments, the Abl TKI is bafetinib.

For the pharmaceutical compositions provided herein, in embodiments the InsR TKI is linsitinib or ceritinib. In embodiments, the InsR TKI is linsitinib. In embodiments, the InsR TKI is ceritinib.

For the pharmaceutical compositions provided herein, in embodiments the c-Kit TKI is pexidartinib, imatinib, or avapritinib. In embodiments, the c-Kit TKI is pexidartinib. In embodiments, the c-Kit TKI is imatinib. In embodiments, the c-Kit TKI is avapritinib.

For the pharmaceutical compositions provided herein, in embodiments the ALK TKI is ceritinib, alectinib, brigatinib, lorlatinib, entrectinib, crizotinib, Tesaro, Teva, or Xcovery. In embodiments, the ALK TKI is ceritinib. In embodiments, the ALK TKI is alectinib. In embodiments, the ALK TKI is brigatinib. In embodiments, the ALK TKI is lorlatinib. In embodiments, the ALK TKI is entrectinib. In embodiments, the ALK TKI is crizotinib. In embodiments, the ALK TKI is TSR-011 (Tesaro). In embodiments, the ALK TKI is CEP-37440 (Teva). In embodiments, the ALK TKI is X-396 (Xcovery).

For the pharmaceutical compositions provided herein, in embodiments the ROS1 TKI is crizotinib, entrectinib, lorlatinib, ceritinib, TPX-0005, DS-6051b, or cabozantinib. In embodiments, the ROS1 TKI is crizotinib. In embodiments, the ROS1 TKI is entrectinib. In embodiments, the ROS1 TKI is lorlatinib. In embodiments, the ROS1 TKI is ceritinib. In embodiments, the ROS1 TKI is TPX-0005. In embodiments, the ROS1 TKI is DS-6051b. In embodiments, the ROS1 TKI is cabozantinib.

For the pharmaceutical compositions provided herein, in embodiments the FGFR TKI is PD173074, dovitinib, Ki23057, lenvatinib, brivanib, nintedanib, ponatinib, MK-2461, lucitanib, or AZD4547. In embodiments, the FGFR TKI is PD173074. In embodiments, the FGFR TKI is dovitinib. In embodiments, the FGFR TKI is Ki23057. In embodiments, the FGFR TKI is lenvatinib. In embodiments, the FGFR TKI is brivanib. In embodiments, the FGFR TKI is nintedanib. In embodiments, the FGFR TKI is ponatinib. In embodiments, the FGFR TKI is MK-2461. In embodiments, the FGFR TKI is lucitanib. In embodiments, the FGFR TKI is AZD4547.

For the pharmaceutical compositions provided herein, in embodiments the HER2 TKI is lapatinib, neratinib, dacomitinib, afatinib, AZD8931, AST1306, AEE788, canertinib, CP724,714, CUDC101, TAK285, aelitinib, or AC480. In embodiments, the HER2 TKI is lapatinib. In embodiments, the HER2 TKI is neratinib. In embodiments, the HER2 TKI is dacomitinib. In embodiments, the HER2 TKI is afatinib. In embodiments, the HER2 TKI is AZD8931. In embodiments, the HER2 TKI is AST1306. In embodiments, the HER2 TKI is AEE788. In embodiments, the HER2 TKI is canertinib. In embodiments, the HER2 TKI is CP724,714. In embodiments, the HER2 TKI is CUDC101. In embodiments, the HER2 TKI is TAK285. In embodiments, the HER2 TKI is aelitinib. In embodiments, the HER2 TKI is AC480.

For the pharmaceutical compositions provided herein, in embodiments the BRAF TKI is vemurafenib, dabrafenib, or encorafenib. In embodiments, the BRAF TKI is vemurafenib. In embodiments, the BRAF TKI is dabrafenib. In embodiments, the BRAF TKI is encorafenib.

For the pharmaceutical compositions provided herein, in embodiments the MAPK TKI is sorafenib, SB590885, PLX4720, XL281, RAF265, encorafenib, dabrafenib, cobimetinib, binimetinib, selumetinib, or trametinib. In embodiments, the MAPK TKI is sorafenib. In embodiments, the MAPK TKI is SB590885. In embodiments, the MAPK TKI is PLX4720. In embodiments, the MAPK TKI is XL281. In embodiments, the MAPK TKI is RAF265. In embodiments, the MAPK TKI is encorafenib. In embodiments, the MAPK TKI is dabrafenib. In embodiments, the MAPK TKI is cobimetinib. In embodiments, the MAPK TKI is binimetinib. In embodiments, the MAPK TKI is selumetinib. In embodiments, the MAPK TKI is trametinib.

For the pharmaceutical compositions provided herein, in embodiments the NTRK TKI is entrectinib or larotrectinib. In embodiments, the NTRK TKI is entrectinib. In embodiments, the NTRK TKI is larotrectinib.

For the pharmaceutical compositions provided herein, in embodiments the RET TKI is nintedanib, vandetanib, or alectinib. In embodiments, the RET TKI is nintedanib. In embodiments, the RET TKI is vandetanib. In embodiments, the RET TKI is alectinib.

For the pharmaceutical compositions provided herein, in embodiments the MET TKI is crizotinib, tivantinib, savolitinib, cabozantinib, foretinib, tepotinib or capmatinib. In embodiments, the MET TKI is crizotinib. In embodiments, the MET TKI is tivantinib. In embodiments, the MET TKI is savolitinib. In embodiments, the MET TKI is cabozantinib. In embodiments, the MET TKI is foretinib. In embodiments, the MET TKI is tepotinib. In embodiments, the MET TKI is capmatinib.

For the pharmaceutical compositions provided herein, in embodiments, the triptolide analog is minnelide, (5R)-5 hydroxy triptolide, 14b-fluoro triptolide, MRx102, or PG490-88. In embodiments, the triptolide analog is minnelide. In embodiments, the triptolide analog is (5R)-5 hydroxy triptolide. In embodiments, the triptolide analog is 14b-fluoro triptolide. In embodiments, the triptolide analog is MRx102. In embodiments, the triptolide analog is PG490-88.

In an aspect is provided pharmaceutical compositions for treating cancer in a subject in need thereof. The TKI in the pharmaceutical composition may be used in an amount typically considered to be a sub-therapeutic amount, but is a therapeutically effective amount when used in combination with triptolide or a triptolide analog, wherein the combination has a synergistic effect. The triptolide in the pharmaceutical composition may be used in an amount typically considered to be a sub-therapeutic amount, but is a therapeutically effective amount when used in combination with a TKI wherein the combination has a synergistic effect. The triptolide analog in the pharmaceutical composition may be used in an amount typically considered to be a sub-therapeutic amount, but is a therapeutically effective amount when used in combination with a TKI wherein the combination has a synergistic effect. In embodiments, the TKI is any TKI described herein, or a combination of two or more TKI described herein. In embodiments the triptolide analog is triptolide analog described herein.

Kits

Provided herein are combination therapy unit dosage forms, where the first and second agents of a combination therapy are present in a unit dosage form. As used herein, the term "unit dosage form" refers to a combination therapy formulation that contains a predetermined dose of a first agent and a predetermined dose of a second agent. The first and second agents of the combination therapy unit dosage form are present in amounts effective to treat the disease for which they are prescribed.

The invention further provides kits comprising a combination therapy as described herein. The kits may contain the first and second agents of the combination therapy as a unit dosage form; e.g., the dosage form contains both the first and second agents; or, as discrete dosage forms (e.g., the first agent is contained in one dosage form and the second agent is contained in another dosage form). The kits can include instructions for use. In one variation, the kits comprise the first and second agents; and instructions for use of in the treatment, prevention, slowing the progression or delaying the onset and/or development of cancer or the recurrence of cancer.

Kits generally comprise suitable packaging. The kits can include one or more containers comprising any compound or combination therapy described herein. Each component (if there is more than one component) can be packaged in separate containers or some components can be combined in one container where cross-reactivity and shelf life permit.

The kits may optionally include a set of instructions, generally written instructions, although electronic storage media (e.g., magnetic diskette or optical disk) containing instructions are also acceptable, relating to the use of component(s) of the methods of the present invention (e.g., treating, preventing and/or delaying the onset and/or the development of a disease being treated. The instructions included with the kit generally include information as to the components and their administration to an individual.

Thus, in an aspect is provided a kit including a first dosage unit form including a tyrosine kinase inhibitor (TKI), a second dosage unit form including triptolide or an analog thereof, and a pharmaceutically acceptable excipient. In embodiments, the TKI is an epithelial growth factor receptor (EGFR) TKI, an anaplastic lymphoma kinase (ALK) TKI, a ROS proto-oncogene 1 (ROS1) TKI, a platelet derived growth factor receptor (PDGFR) TKI, a vascular endothelial growth factor receptor (VEGFR) TKI, an insulin receptor (InsR) TKI, a Src TKI, a c-Kit TKI, a fibroblast growth factor receptor (FGFR) TKI, a human epidermal growth factor receptor 2 (HER2) TKI, a B-Raf proto-oncogene (BRAF) TKI, a mitogen-activated protein kinase (MAPK) TKI, a neurotrophin tyrosine kinase receptor (NTRK) TKI, a RET proto-oncogene (RET) TKI, a mesenchymal-epithelial transition factor receptor (MET) TKI, or an Abl TKI. In embodiments, the TKI is an EGFR TKI. In embodiments, the EGFR TKI is Osimertinib (Tagrisso), Erlotinib (Tarceva), Gefitinib, or Afatinib. In embodiments, the EGFR TKI is Osimertinib. In embodiments, the triptolide analog is minnelide, (5R)-5 hydroxy triptolide, 14b-fluoro triptolide, MRx102 or PG490-88. In embodiments, the triptolide analog is minnelide.

EXAMPLES

Background to Studies Provided Herein

Non-small cell lung cancers (NSCLCs) harboring EGFR activating mutations initially respond to treatment with EGFR tyrosine kinase inhibitors (EGFR-TKIs), including Tagrisso (osimertinib). However, acquired resistance to EGFR-TKIs develops in almost all patients, most commonly due to new DNA mutations that arise during treatment. Without wishing to be bound by scientific theory, previous studies conducted by the inventors indicate that inhibition of tyrosine kinase activity with TKI's are responsible for the degradation of Heat Shock Protein 72 (HSP72). HSP72 plays an important role in editing DNA replication errors; thus, treatment with TKIs such as Tagrisso may result in increases in DNA mutation rates that contribute to drug resistance and disease progression.

Example 1: Studies Including Velcade

The inventors sought to maintain high levels of HSP72 while sustaining cancer treatment with TKIs. Velcade (Bortezomib), an FDA-approved drug, was tested to block the HSP72 degradation that occurs with Tagrisso. Results showed that Velcade effectively maintains high levels of HSP72 protein in Tagrisso-treated HCC827 cells.

Subsequently, inventors evaluated the time period in which cancer cells develop resistance to Tagrisso, and whether Velcade affects resistance development. In the absence of Velcade, HCC827 cells developed resistance to Tagrisso within 29 days, when treated with a dose comparable to the recommended dosage administered to human patients. However, in the presence of Velcade, HCC827 cells remained sensitive to Tagrisso after 60 days of drug treatment when administered the same concentration as described above. As illustrated in FIG. 1, these results show that Velcade may effectively suppress Tagrisso resistance in HCC827 cells.

A mouse model was then used to determine the efficacy of Velcade in suppressing Tagrisso resistance and in sensitizing lung cancer tumors to Tagrisso. To model human EGFR mutated NSCLC, HCC827 cells were grafted into mice. The HCC827 grafted mice were divided into five treatment groups including: DMSO vehicle control/no treatment (Group 1); Tagrisso treatment (Group 2), Velcade treatment (Group 3), Tagrisso+Velcade (Group 4), and Tagrisso treatment where Velcade will be administered once Tagrisso resistance is observed (Group 5).

Figure 2:
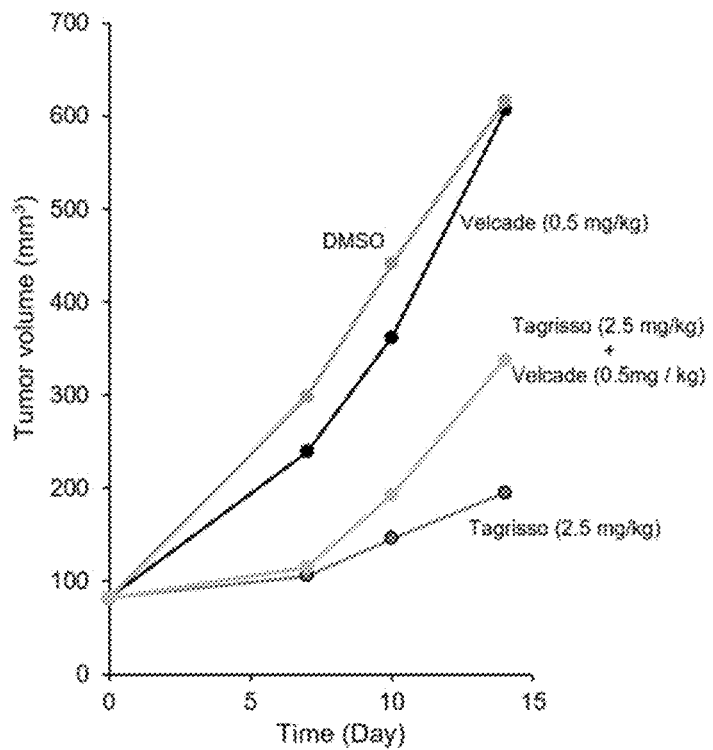
FIG. 2 is a graph showing the effect of Velcade, Tagrisso+Velcade, and Tagrisso, on tumor growth. DMSO was used as a vehicle control.

Compared to the untreated control (Group 1), Tagrisso administered at a dose corresponding the recommended dose administered to human patients reduced tumor size and blocked tumor growth (Group 2). Conversely, a low dose of Velcade moderately inhibited tumor growth (Group 3). There was no further inhibition of tumor growth observed in mice treated with a combination of Tagrisso and Velcade (Group 4), compared to Group 2. These results indicate that the combination of Velcade and Tagrisso does not provide additional anti-tumor effects compared to Tagrisso alone, as illustrated in FIG. 2. Since Tagrisso remained effective at the time of this analysis and no resistance was observed, it was premature to assess the effect of Velcade on Tagrisso resistant cells (Group 5).

Figure 3:
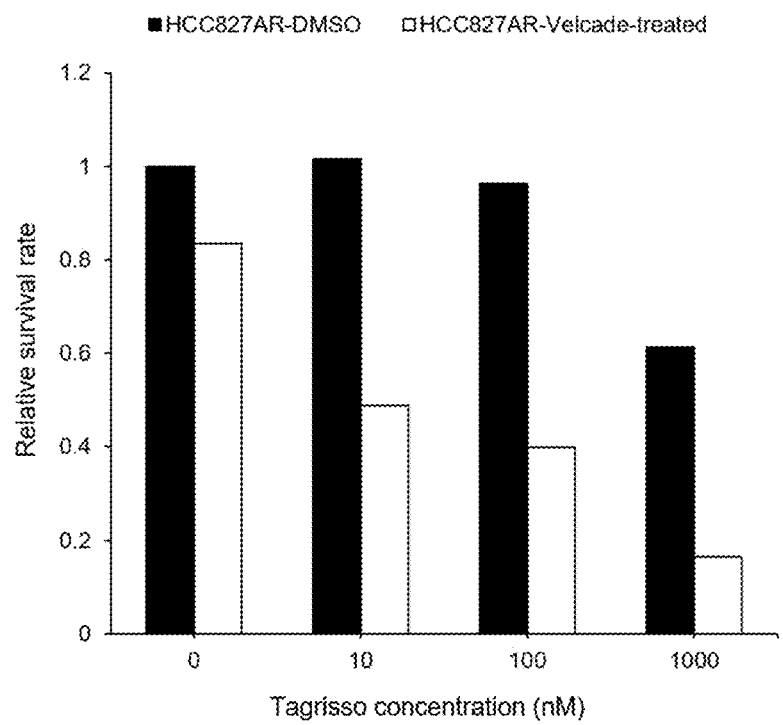
FIG. 3 is a bar graph showing survival rates of groups of HCC827-grafted mice treated with varying concentrations of Tagrisso in combination with a fixed concentration of Velcade. DMSO was used as a vehicle control.

Further, the effect of Velcade on survival rates of Tagrisso treated mice was evaluated. HCC827-grafted mice were divided into groups and each group of mice was treated with 0 to 1000 nM of Tagrisso, and with or without co-administered Velcade. As shown in FIG. 3, Velcade did not improve survival of the mice. In fact, mice treated with Tagrisso and Velcade showed lower survival rates than mice treated with Tagrisso alone.

A separate experiment was completed using PC9-grafted mice in the same treatment setting as previously described. PC9 tumors were shown to grow faster than the HCC827 tumors. Velcade had little inhibitory effect on PC9 tumor growth, compared to the untreated control. The PC9 tumors in mice treated with Velcade and Tagrisso showed similar growth compared to tumors in mice treated with Tagrisso alone. Velcade treatment additionally caused skin inflammation after one month, and the experiment was subsequently terminated.

Example 2: Studies Including Triptolide

Figure 4:
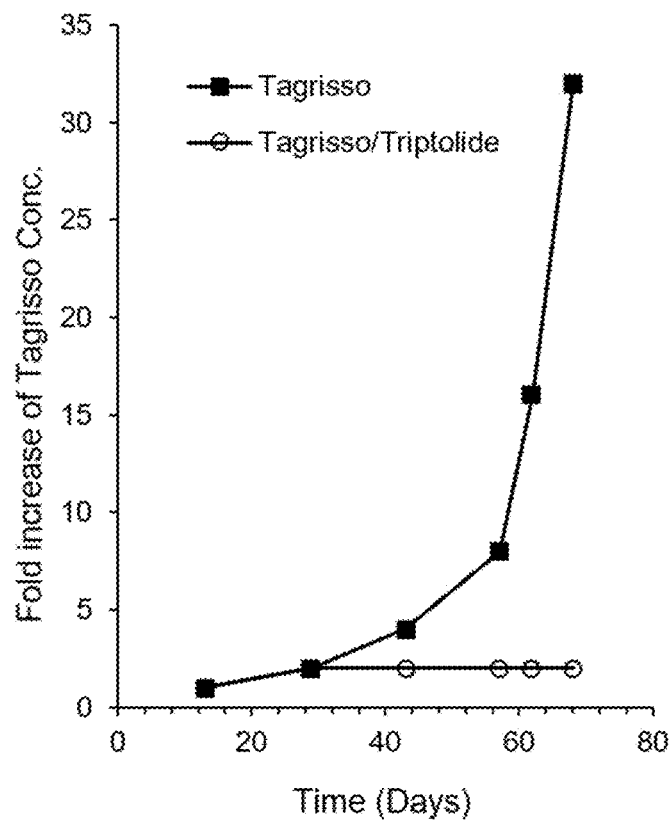
FIG. 4 is a graph showing the effect of Triptolide on Tagrisso resistance development.

Inventors observed that another medicinal compound, Triptolide, may activate HSP72 cellular expression. Triptolide by itself is a potent anti-tumor agent and functions by activating tumor suppressor protein p53 and blocking tumor promotor NF-κB. In cell culture experiments, inventors found that Triptolide and Tagrisso display a potentiation effect in killing HCC827 non-small cell EGFR mutant lung carcinoma cells. Inventors monitored the time for which cancer cells developed resistance to Tagrisso in the absence or presence of Triptolide. As illustrated in FIG. 4, HCC827 cells maintained sensitivity to Tagrisso in the presence of Triptolide throughout the 70 day duration of the study, compared to 29 days for resistance to develop when treated with Tagrisso alone. These results indicate that Triptolide has anti-tumor effects in non-small cell EGFR mutant lung carcinoma cells and can suppress Tagrisso resistance on the cellular level.

Figure 5A:
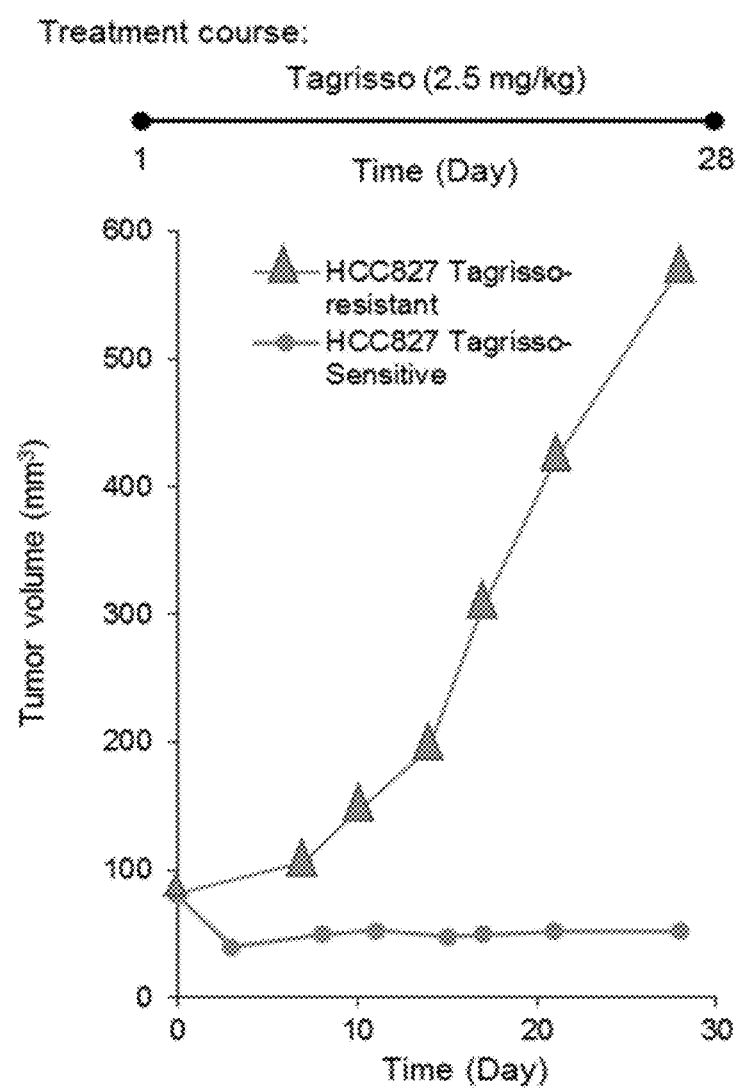
FIG. 5A is a graph illustrating the effect of Tagrisso on tumor growth in HCC827 cells and HCC827 Tagrisso-resistant cells. The triangle data markers represent data for HCC827-Tagrisso-resistant cells and the circle data markers represent data for HCC827 cells, which have not developed resistance to Tagrisso.
Figure 5B:
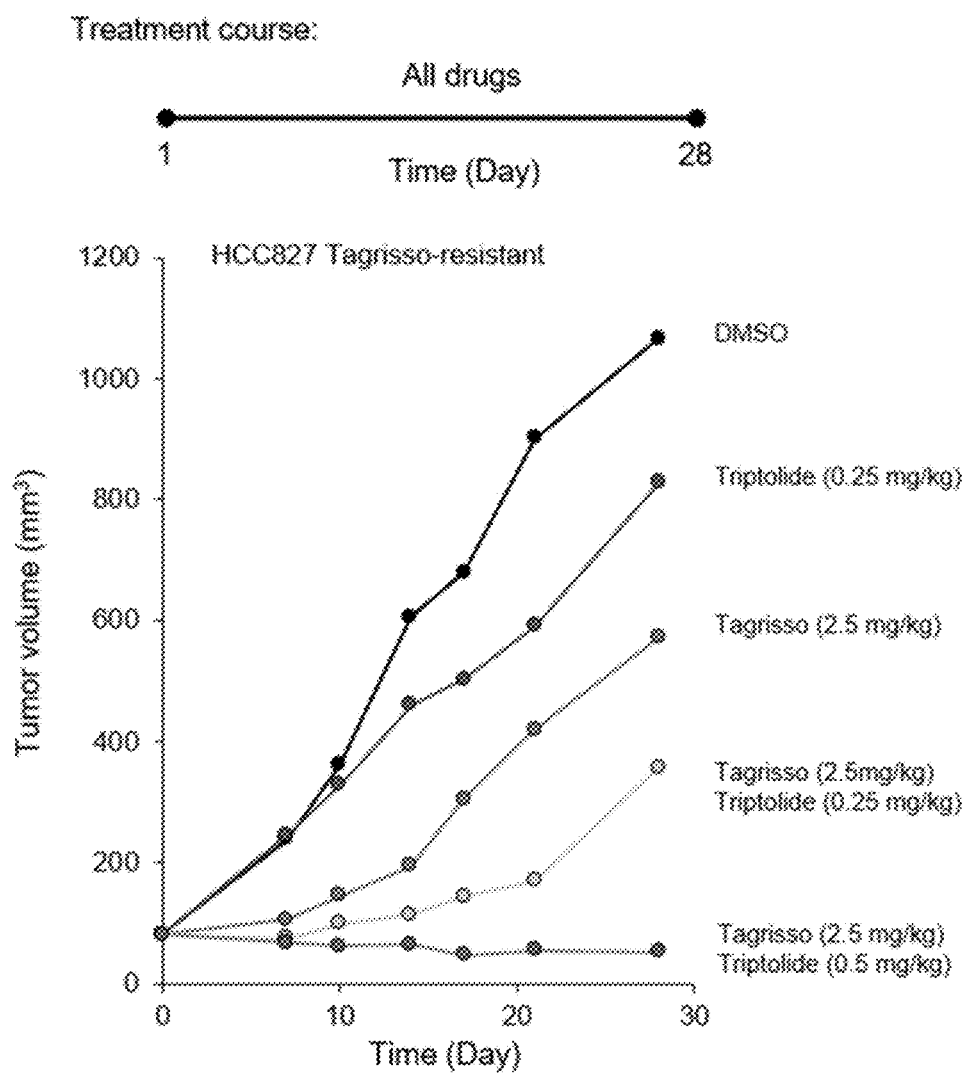
FIG. 5B is a graph illustrating the effect of Triptolide, Tagrisso, and Tagrisso+Triptolide on HCC827 Tagrisso-resistant tumor growth. Dosages of each treatment were administered as indicated, and DMSO was used as a vehicle control.

Furthermore, inventors tested whether triptolide can sensitize EGFR-TKI-resistant lung cancer cells to Tagrisso in human cancer cell grafted mouse models. Results illustrated in FIG. 5A show that Tagrisso does not reduce tumor growth in EGFR-TKI resistant HCC827 lung cancer cells. As expected, tumor growth is inhibited in non-resistant HCC827 cells. Inventors then treated TKI-resistant HCC827 cells with Tagrisso in the absence or presence of Triptolide. Results shown in FIG. 5B indicate that Triptolide sensitizes Tagrisso-resistant HCC827 cells to the EGFR-TKI. Triptolide in combination with Tagrisso reduces tumor growth more than treatment with Tagrisso or Triptolide alone. These findings show that triptolide may suppress EGFR mutated NSCLCs to develop drug resistance and break the drug resistance as well.

Figure 6:
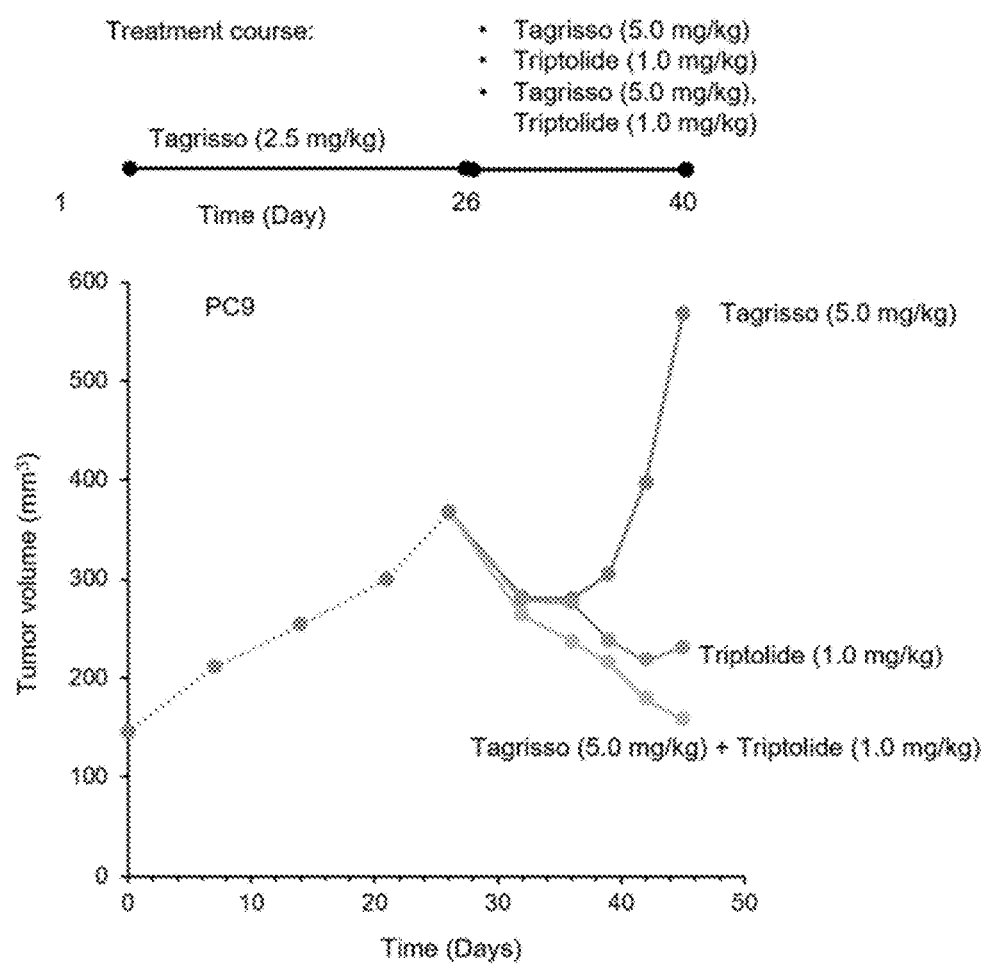
FIG. 6 is a graph showing the effect of Tagrisso, Triptolide, and Tagrisso+Triptolide on PC9 tumor growth following Tagrisso resistance development. Dosages of each treatment are as indicated.

Inventors further tested whether Triptolide can sensitize lung cancer cells to Tagrisso in the human cancer cell grafted mouse models. PC9-grafted mice were treated with Tagrisso for 4 weeks, at which Tagrisso began to lose its inhibitory effect on the PC9 tumor. The grafted mice were then divided into three groups: Tagrisso (2× dosage) (Group 1), Triptolide (Group 2), Tagrisso and Triptolide (Group 3). Inventors observed that doubling the Tagrisso dosage resulted in a brief inhibitory effect on PC9 tumor growth for one week, after which Tagrisso lost its inhibitory effect on tumor growth. However, Triptolide consistently inhibited PC9 tumor growth for at least 4 weeks, as illustrated in FIG. 6. Combined administration of triptolide and Tagrisso (Group 3) drove tumor volume down to 40% of its volume prior to the combined treatment (100%). Alternatively, tumor volumes after Tagrisso (Group 1) or Triptolide (Group 2) treatments were 190% and 60%, respectively. These observations suggest that Triptolide may be used to treat Tagrisso-resistant lung cancer cells.

Figure 7:
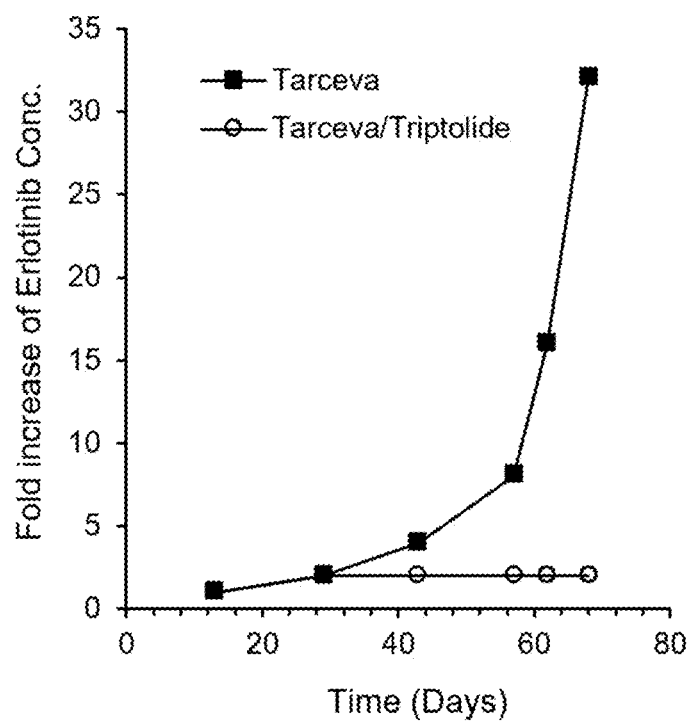
FIG. 7 is a graph showing the effect of Triptolide on Tarceva (Erlotinib) resistance development in a grafted tumor model.

Inventors evaluated the effect of Triptolide on Tarceva (erlotinib) resistance development in HCC827 cells. Inventors determined the timeframe in which cancer cells developed resistance to Tarceva in the absence or presence of Triptolide. As illustrated in FIG. 7, HCC827 cells developed resistance to Tarceva in about 30 days, while HCC827 cells maintained sensitivity to Tarceva when also treated with Triptolide, and resistance was not observed during the 70 day duration of the study. These results indicate that Triptolide has anti-tumor effects and can suppress Tarceva resistance on the cellular level.

Example 3: Materials and Methods

Cell Culture, Drug Treatment, and Cell Viability Assays
EGFR mutated NSCLC cancer cell line HCC827 or AZD9291 (Tagrisso) resistant HCC827 cells were cultured in H1640 medium supplemented with 10% FBS and 1% penicillin/streptomycin. AZD9291 (>99.95%) was purchased from MedChemExpress. Triptolide (>98%) was from the Lingonberry Group, Hei Long Jiang, China). To measure the viability of HCC827 cells in the absence or presence of AZD9291 and/or triptolide, $10^4$ cells per well were seeded in a 6-well plate and incubated in culture medium containing DMSO or drugs. The medium was replaced with fresh medium with corresponding drugs every two days. After one week culture, the viable cells in each well of the plate was measured by cell counting. For the drug resistance assay, once the viable cells in a drug-treated well is more than 50% of the viable of the control, the AZD9291 concentration was doubled in the next round treatment.

Tumor Grafting and Drug Treatment of NOD/SCID Mice
HCC827 or AZD9291-resistant HCC827 cancer or PC9 NSCLC cells ($5\times10^6$) were subcutaneously injected into NOD/SCID mice (2 months old, n=6-10 for each group). After tumor size reaches approximately 100 mm³, the mice were administered AZD9291 individually or in combination with triptolide using ALZET osmotic pump, which was implanted under the skin of the mice for a specific time period. The tumor volume was monitored twice a week for 4-8 weeks. All protocols involving animals were approved by the Research Animal Care Committee of City of Hope, in compliance with the Public Health Service Policy of the United States.

It is understood that the examples and embodiments described herein are for illustrative purposes only and that various modifications or changes in light thereof will be suggested to persons skilled in the art and are to be comprised within the spirit and purview of this application and scope of the appended claims. All publications, patents, and patent applications cited herein are hereby incorporated by reference in their entirety for all purposes.

What is claimed is:
1. A method of treating an Osimertinib resistant cancer in a subject in need thereof, the method comprising administering to said subject a therapeutically effective amount of a tyrosine kinase inhibitor (TKI) and triptolide or an analog thereof, wherein said TKI is Osimertinib and said triptolide analog is minnelide.

2. The method of claim 1, wherein said cancer is breast cancer, colon cancer, lung cancer, leukemia, thyroid cancer, liver cancer, melanoma, skin cancer, kidney cancer, bladder cancer or head and neck cancer.

3. A method of preventing resistance to a tyrosine kinase inhibitor (TKI) in a subject having cancer, the method comprising administering to said subject triptolide or an analog thereof, wherein the triptolide analog is minnelide.

4. The method of claim 3, wherein said TKI is an epithelial growth factor receptor (EGFR) TKI.

5. The method of claim 4, wherein said EGFR TKI is Osimertinib.

6. The method of claim 3, further comprising administering to said subject said tyrosine kinase inhibitor.

7. The method of claim 3, wherein said cancer is breast cancer, colon cancer, lung cancer, leukemia, thyroid cancer, liver cancer, melanoma, skin cancer, kidney cancer, bladder cancer or head and neck cancer.

8. A pharmaceutical composition comprising a tyrosine kinase inhibitor (TKI), triptolide or an analog thereof, and a pharmaceutically acceptable excipient, wherein said TKI is Osimertinib and said triptolide analog is minnelide.

9. A kit comprising a first dosage unit form comprising a tyrosine kinase inhibitor (TKI), a second dosage unit form comprising triptolide or an analog thereof, and a pharmaceutically acceptable excipient, wherein said TKI is Osimertinib and said triptolide analog is minnelide.

* * * * *